United States Patent
Hwang et al.

(10) Patent No.: US 9,963,701 B2
(45) Date of Patent: May 8, 2018

(54) PHARMACEUTICAL COMPOSITION FOR TREATMENT OF RADIATION- OR DRUG-RESISTANT CANCER COMPRISING HRP-3 INHIBITOR

(71) Applicant: KOREA INSTITUTE OF RADIOLOGICAL & MEDICAL SCIENCES, Seoul (KR)

(72) Inventors: Sang Gu Hwang, Seoul (KR); Hong Shik Yun, Seoul (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 0 days. days.

(21) Appl. No.: 15/025,872

(22) PCT Filed: Sep. 4, 2014

(86) PCT No.: PCT/KR2014/008327
§ 371 (c)(1),
(2) Date: Mar. 29, 2016

(87) PCT Pub. No.: WO2015/046783
PCT Pub. Date: Apr. 2, 2015

(65) Prior Publication Data
US 2016/0298119 A1    Oct. 13, 2016

(30) Foreign Application Priority Data
Sep. 30, 2013    (KR) .......................... 10-2013-0116450

(51) Int. Cl.
| | |
|---|---|
| C12N 15/11 | (2006.01) |
| C07H 21/04 | (2006.01) |
| C12N 15/113 | (2010.01) |
| A61K 31/475 | (2006.01) |
| A61K 31/704 | (2006.01) |
| A61K 31/7088 | (2006.01) |
| A61K 39/395 | (2006.01) |
| A61K 45/06 | (2006.01) |
| C07K 16/22 | (2006.01) |
| A61K 39/00 | (2006.01) |

(52) U.S. Cl.
CPC ........ *C12N 15/1136* (2013.01); *A61K 31/475* (2013.01); *A61K 31/704* (2013.01); *A61K 31/7088* (2013.01); *A61K 39/3955* (2013.01); *A61K 45/06* (2013.01); *C07K 16/22* (2013.01); *A61K 2039/505* (2013.01); *C07K 2317/76* (2013.01); *C12N 2310/14* (2013.01); *C12N 2320/31* (2013.01)

(58) Field of Classification Search
None
See application file for complete search history.

(56) References Cited

U.S. PATENT DOCUMENTS

| | | | | |
|---|---|---|---|---|
| 5,595,756 A | * | 1/1997 | Bally | ............ A61K 9/1272 264/4.1 |
| 2011/0190445 A1 | * | 8/2011 | Anro | ............ C12N 15/115 525/54.2 |

FOREIGN PATENT DOCUMENTS

| | | |
|---|---|---|
| KR | 10-2011-0088771 A | 8/2011 |
| KR | 10-2011-0139397 A | 12/2011 |
| WO | WO2009/149921 A2 | 12/2009 |
| WO | WO2011/031842 A1 | 3/2011 |
| WO | WO2011/031890 A2 | 3/2011 |

OTHER PUBLICATIONS

Aagaard et al. RNAi therapeutics: principles, prospects and challenges. Advanced Drug Delivery Reviews 59 (2007) 75-86.*
Warzocha et al. Antisense strategy:biological utility and prospects in the treatment of hematological malignancies. Leukemia and Lymphoma, vol. 24. pp. 267-281.*
Vajdos et al. Comprehensive Functional Maps of the Antigen-binding Site of an Anti-ErbB2 Antibody Obtained with Shotgun Scanning Mutagenesis. Journal of Molecular Biology Jul. 5, 2002;320(2):415-28 at 416.*
Brown et al. Tolerance to Single, but Not Multiple, Amino Acid Replacements in Antibody VH CDR2. Journal of Immunology, May 1996; 156(9):3285-91.*
Yun et al. Depletion of hepatoma-derived growth factor-related protein-3 induces apoptotic sensitization of radioresistant A549 cells via reactive oxygen species-dependent p53 activation. Biochemical and Biophysical Research Communications, 2013; 439(3): 333-339.*
Xiao et al. HDGF-related protein-3 is required for anchorage-independent survival and chemoresistance in HCC. Gut, published online Apr. 5, 2012; 62(3):440-51.*
Heppner et al. Tumor heterogeneity: biological implications and therapeutic consequences. Cancer Metastasis Review 2:5-23; 1983.*

(Continued)

*Primary Examiner* — Vanessa L. Ford
*Assistant Examiner* — Sandra E Dillahunt
(74) *Attorney, Agent, or Firm* — Greer, Burns & Crain; Gregory P. Einhorn

(57) ABSTRACT

The present invention relates to a pharmaceutical composition for treating a radiation- or drug-resistant cancer, containing an agent capable of inhibiting the expression of hepatoma-derived growth factor (HDGF)-related protein-3 (HRP-3), a method of treating a radiation- or drug-resistant cancer by administering the pharmaceutical composition, and the use of an HRP-3 inhibitor for preparing an agent for treating a radiation- or drug-resistant cancer. The use of the pharmaceutical composition of the present invention enables to treat a resistant cancer in combination with a conventional anticancer chemotherapy or radiotherapy. Accordingly, the pharmaceutical composition of the present invention can reduce both the costs for developing anticancer agents against resistant cancers and the costs for treating cancers in patients, thus being useful for the economic and effective treatment of resistant cancers.

10 Claims, 33 Drawing Sheets

(56) References Cited

OTHER PUBLICATIONS

Jain RK. Barriers to drug delivery in solid tumors. Scientific American, Jul. 1994, 58-65.*
Yun, et al., "Depletion of hepatoma-derived growth factor-related protein-3 induces apoptotic sensitization of radioresistant A549 cells via reactive oxygen species-dependent p53 activation", Biochemical and Biophysical Research Communications, Sep. 2013, vol. 439, pp. 333-339.
Xiao, et al., "HGDF-related protein-3 is required for anchorage-independent survival and chemoresistance in hepatocellular carcinomas", GUT, Apr. 2012, vol. 62, pp. 440-451.
Yun, et al., "Knockdown of hepatoma-derived growth factor-related protein-3 induces apoptosis of H1299 cells via ROS-dependent and p53-independent NF-jB activation", Biochemical and Biophysical Research Communications, May 2014, vol. 449, pp. 471-476.
Written Opinion for PCT/KR2014/008327, filed Sep. 4, 2014, dated Dec. 24, 2014.
International Search Report for PCT/KR2014/008327, filed Sep. 4, 2014, dated Dec. 24, 2014.

\* cited by examiner

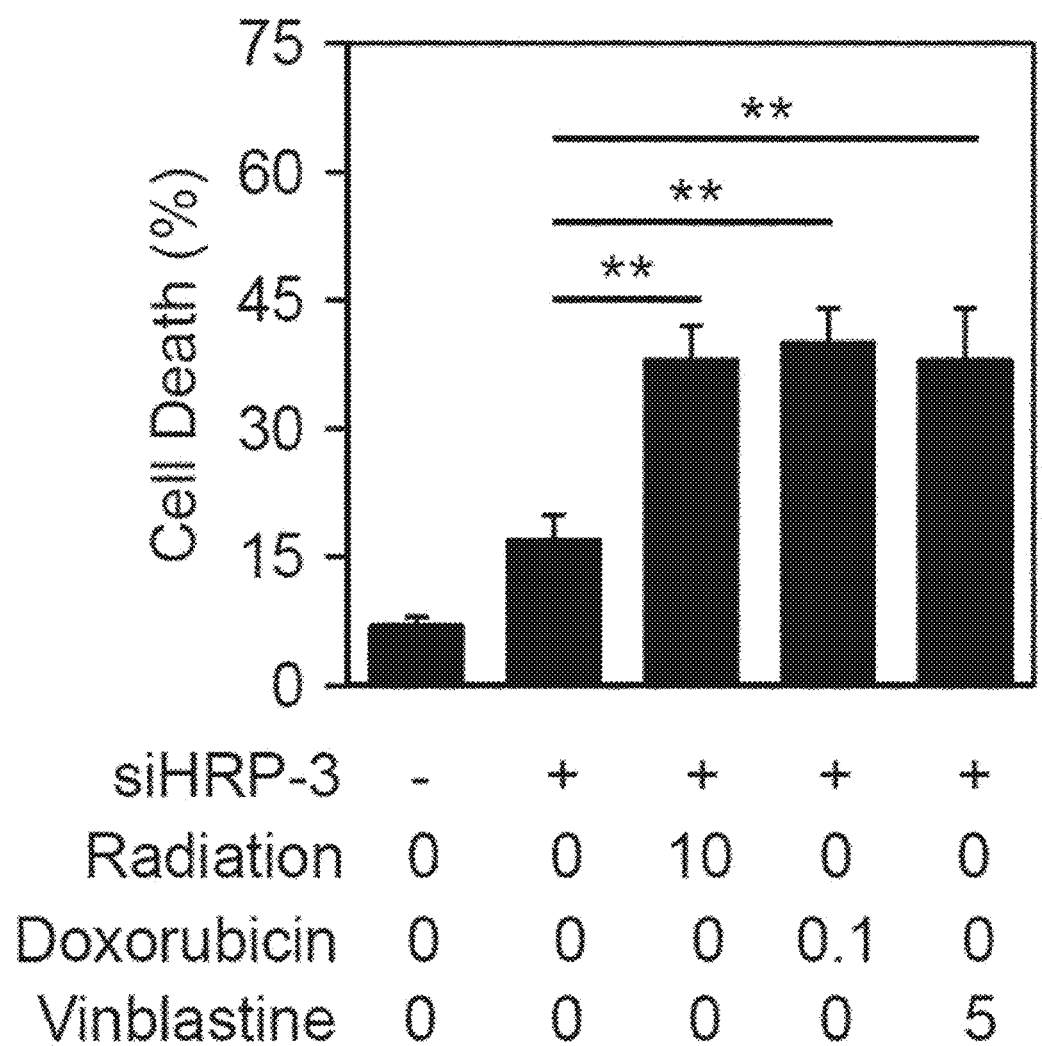

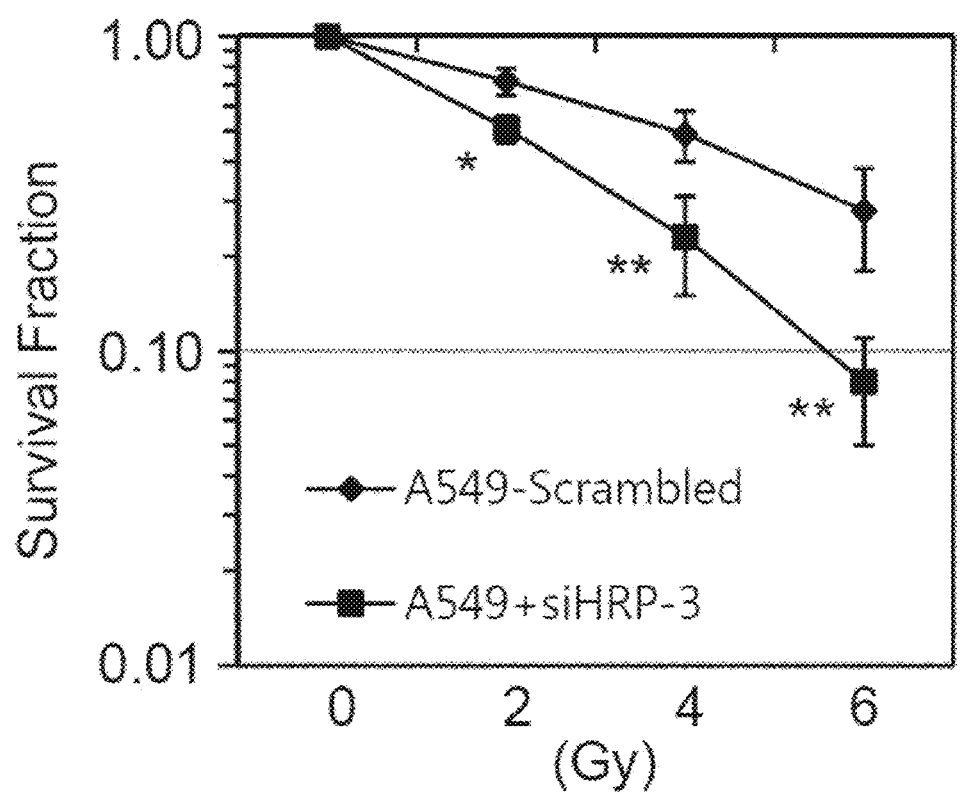

PHARMACEUTICAL COMPOSITION FOR TREATMENT OF RADIATION- OR DRUG-RESISTANT CANCER COMPRISING HRP-3 INHIBITOR

RELATED APPLICATIONS

This application is a national phase application claiming benefit of priority under 35 U.S.C. § 371 to International (PCT) Patent Application serial number PCT/KR2014/008327, filed Sep. 4, 2014, which claims benefit of priority to Korean Application 10-2013-0116450, filed Sep. 30, 2013. The aforementioned applications are expressly incorporated herein by reference in their entirety and for all purposes.

TECHNICAL FIELD

The present invention relates to a pharmaceutical composition for treating a radiation- or drug-resistant cancer, which includes an agent capable of inhibiting the expression of hepatoma-derived growth factor (HDGF)-related protein-3 (HRP-3), and more particularly to a pharmaceutical composition for treating a radiation- or drug-resistant cancer, which includes a therapeutic agent capable of inhibiting the expression of HRP-3, a method of treating a radiation- or drug-resistant cancer by administering the pharmaceutical composition, and the use of an HRP-3 inhibitor for preparing an agent to treat a radiation- or drug-resistant cancer.

BACKGROUND

Main methods used for cancer treatment include surgery, anticancer chemotherapy, radiotherapy, etc. Among them, surgery and radiotherapy are local therapies showing effects only in excised or irradiated areas, and anticancer chemotherapy is a systemic therapy showing effects throughout the body. Most cancers occur locally and metastasize systemically. In many cases, cancers are diagnosed after metastasis unless diagnosed very early. Accordingly, cancers often recur even after an effective local therapy. Thus, for most cancer treatment, local therapy is used together with anticancer chemotherapy to improve effectiveness against systemically spread cancer.

Administration of anticancer therapy drugs is important for removing either a very small cancer tissue difficult to observe visually after surgical removal of cancer sites, or cancer cells metastasized from a primary site to other tissues. However, when a cancer is resistant to a specific anticancer drug, or a specific anticancer drug is administered long term cancer cells may acquire drug resistance and thus anticancer effects may not be sufficient. Known anticancer drugs to which cancer cells can acquire resistance mainly include hydrophilic and amphiphilic drugs, for example, taxane, vinca alkaloid drugs (vinorelbine, vincristine, and vinblastine), anthracycline drugs (doxorubicin, daunorubicin, and epirubicin), epidophyllotoxin (etoposide, and teniposide), antimetabolites (methorexate, fluorouracil, cytosar, 5-azacytosine, 6-mercaptopurine, and gemcitabine), topotecan, dactinomycin, mitomycin, etc. The problem that cancer cells acquire resistance to anticancer drugs in anticancer therapy has long been a great obstacle in treating tumors.

Various studies have been conducted to resolve this obstacle. For example, Korean Patent Application Publication No. 2011-88771 discloses a method of treating cancer resistant to cetuximab or gefitinib by administering a PI3K/Akt inhibitor in combination with cetuximab or gefitinib. Korean Patent Application Publication No. 2011-139397 discloses a method of preventing or treating anticancer drug-resistant cancers using 5,6-benzoflavone compounds, and WO 2011/031842 discloses a method of using N-(4-((3-(2-amino-4-pyrimidinyl)-2-pyridinyl)oxy)phenyl)-4-(4-methyl-2-thienyl)-1-phthalazinamine or a pharmaceutically acceptable salt thereof, to treat solid tumors that have become resistant to treatment with chemotherapeutic agents. In addition, WO 2011/031890 discloses a method of treating drug-resistant cancers by administering a therapeutically effective amount of sodium meta-arsenite to a subject in need thereof. However, such methods for treating drug-resistant cancers have a shortcoming that they can be applied only to patients satisfying specific conditions, and thus cannot be effectively applied to treat general drug-resistant cancers.

At present, to increase the treatment rate for cancers, there is a need to expand radical surgery by early diagnosis and develop a method of effectively using anticancer chemotherapy for patients who cannot undergo surgery or patients who have a high risk of recurrence after surgery. In order to develop the therapeutic method, the mechanism of cancer cells' resistance to anticancer drugs should be elucidated, and based on the finding, a method of overcoming the anticancer drug-resistance of cancer cells should be developed. However, the studies still remain in their early stage.

DISCLOSURE OF INVENTION

The present inventors have made extensive efforts to develop a method capable of more effectively treating cancer patients having resistant cancer, and have found that HRP-3 protein expressed in non-small-cell lung cancer causes cancer cells to be resistant to anticancer drugs, and thus the inhibition of HRP-3 expression in cancer cells can suppress cancer cells' resistance to anticancer drugs, thereby completing the present invention.

An objective of the present invention is to provide a pharmaceutical composition for treating a radiation- or drug-resistant cancer, which includes an agent capable of inhibiting the expression of HRP-3.

Another objective of the present invention is to provide a method of treating a radiation- or drug-resistant cancer by administering the pharmaceutical composition.

Still another objective of the present invention is to provide the use of an agent capable of inhibiting the expression of HRP-3 for preparing the pharmaceutical composition.

Advantageous Effects of Invention

Use of the pharmaceutical composition of the present invention enables resistant cancer to be treated using a conventional anticancer chemotherapy or radiotherapy. Accordingly, the pharmaceutical composition of the present invention can reduce not only the costs of developing anticancer agents against resistant cancers, but also the costs of treating cancer in patients, thus being widely applicable to the economic and effective treatment of resistant cancer.

BRIEF DESCRIPTION OF THE DRAWINGS

FIG. 1A: H460 and A549 cells were placed with 10 Gy of radiation, 0.1 μg/ml of doxorubicin or 5 ng/ml of vinblastine for 48 hours. Apoptosis was determined by FACS analysis, and data are expressed as mean±SD. FIG. 1B: The transcript and protein levels of HRP-3 in H460 and A549 cells were determined by RT-PCR and Western blot. FIG. 1C: Confocal microscope images of HRP-3 localization in H460 and A549 cells.

(FIGS. 2A and 2B) A549 cells were transfected with 100 nM scrambled, HRP-3 siRNA #1 or HRP-3 siRNA #2 for 48 hours. HRP-3 mRNA and protein levels were determined by qRT-PCR (FIG. 2A) and Western blotting (FIG. 2B). (FIGS. 2C-F) A549 cells were transfected with 100 nM scrambled siRNA or HRP-3 siRNA for 4 days (FIG. 2C), 2 days (FIGS. 2C and 2D) and 14 days (FIG. 2F). Proliferation was determined by cell counting, and data are expressed as mean±SD (FIG. 2C). Changes in cell morphology were observed by an optical microscope (FIG. 2D, left; scale bar: 1 mm), and apoptosis was determined by FACS analysis; data are expressed as means±SD (FIG. 2D, right). Two apoptotic markers were detected by Western blotting (FIG. 2E). Colony formation was visualized by trypan blue staining (FIG. 2F, left), and data are expressed as mean±SD (FIG. 2F, right).

FIGS. 3A-F show the synergistic effect of HRP-3 depletion on apoptosis in A549 cells treated with radiation or anticancer drugs. (FIG. 3A) A549 cells were treated with 10 Gy radiation (top), 0.1 µg/ml doxorubicin (middle) or 5 ng/ml vinblastine (bottom) for the indicated times. HRP-3 protein levels were determined by Western blotting. (FIG. 3B) A549 cells were transfected with 100 nM scrambled siRNA or HRP-3 siRNA, and then treated with 10 Gy radiation (top), 0.1 µg/ml doxorubicin (middle) or 5 ng/ml vinblastine (bottom) for the indicated times. Apoptotic rate was determined by FACS analysis, and data are expressed as mean±SD. (FIGS. 3C and 3D) A549 cells were transfected with 100 nM scrambled siRNA or HRP-3 siRNA, and then treated with radiation ranging from 0 to 6 Gy for 14 days. Images of colony formation were visualized by trypan blue staining (FIG. 3C, left), and data are expressed as mean±SD (FIG. 3C, right). Survival fraction determined by colony analysis is presented as a survival curve, and data are expressed as mean±SD (FIG. 3D). (FIGS. 3E and 3F) A549 cells were transfected with 100 nM scrambled siRNA or HRP-3 siRNA, and then treated with 10 Gy radiation (3E), 0.1 µg/ml doxorubicin (middle) and 5 ng/ml vinblastine (FIG. 3F) for 48 hours. Two apoptotic markers were determined by Western blotting.

(FIG. 4A) The levels of Nrf2, HO-1, Keap-1 and HRP-3 proteins in H460 and A549 cells were determined by Western blotting. (FIG. 4B) A549 cells were transfected with 100 nM scrambled siRNA or HRP-3 siRNA for 48 hours. The levels of Nrf2, HO-1, Keap-1 and HRP-3 proteins were determined by Western blotting. (FIG. 4C) A549 cells were incubated without or with 1 mM NAC as a ROS scavenger, and then transfected with 100 nM scrambled siRNA or HRP-3 siRNA for 48 hours. ROS production was assessed by FACS analysis using 10 nM DCF-DA, and data are expressed as means±SD. (FIG. 4D) A549 cells were transfected with 100 nM scrambled siRNA or HRP-3 siRNA without or with exposure to 10 Gy radiation. ROS production was assessed by FACS analysis using 10 nM DCF-DA, and data are expressed as mean±SD.

(FIGS. 5A and 5B) A549 cells were transfected with 100 nM scrambled siRNA or HRP-3 siRNA in the absence (FIG. 5A) or presence (FIG. 5B) of 1 mM NAC. The levels of HRP-3, cleaved PARP, p53, pp53 and PUMA proteins were detected by Western blotting. (FIG. 5C) A549 cells were transfected with 100 nM scrambled siRNA or HRP-3 siRNA for 48 hours, and then treated with 10 µM cycloheximide for the indicated times. The levels of HRP-3, p53 and pp53 proteins were determined by Western blotting (left), and the half-life of proteins is presented graphically (right). Data are expressed as mean±SD. The level of p53 mRNA was detected by RT-PCR (left). (FIG. 5D) A549 cells were transfected with 100 nM scrambled siRNA or HRP-3 siRNA without or with exposure to 10 Gy radiation for 48 hours. The levels of HRP-3, cleaved PARP, p53, pp53 and PUMA proteins were detected by Western blotting.

(FIG. 6A) Oncomine database was queried for the HRP-3 expression in the available datasets based on the cancer vs. normal cells (threshold p-value: 1E-4, and fold change: 2). 0: normal cell, 1: lung adenocarcinoma cell, 2: lung carcinoid tumor cell, 3: small cell lung carcinoma cell, and 4: squamous cell carcinoma cell. (FIG. 6B) The transcript and protein levels of HRP-3 in lung cancer cells were determined by quantitative real-time PCR (up) and Western blotting (bottom), respectively. (FIG. 6C) Confocal images of HRP-3 localization in H460 and H1299 cells (scale bar: 50 µm). (FIGS. 6D and 6E) H1299 cells were treated with 10 Gy radiation, 0.1 µg/ml doxorubicin, or 5 ng/ml vinblastine for the indicated times. The protein level and localization of HRP-3 were determined by Western blotting (FIG. 6D) and laser scanning confocal microscope (FIG. 6E, scale bar: 50 µm), respectively.

(FIG. 7A) H460 and H1299 cells were treated with 10 Gy radiation, 0.1 µg/ml doxorubicin, or 5 ng/ml vinblastine for 48 hours. Apoptosis was determined by FACS analysis and data are expressed as means±SD (p<0.005, and *p<0.0005 compared with untreated controls). (FIGS. 7B and 7C) H1299 cells were transfected with 100 nM scrambled siRNA or HRP-3 siRNA (siHRP-3) for 5 hours and then cultured for additional 4 days (FIG. 7B) or 2 days (FIG. 7Cc). Proliferation was determined by cell counting and data are expressed as means±SD (*p<0.05 and p<0.005 compared with controls) (FIG. 7B), and the protein levels of two apoptosis markers were detected by Western blotting (FIG. 7C). (FIG. 7D) H1299 cells were transfected with 100 nM scrambled siRNA or HRP-3 siRNA (siHRP-3) and then left untreated, or treated as in (FIG. 7A). Apoptosis was determined by FACS analysis, and data are expressed as means±SD (p<0.005 compared with cells transfected with siHRP-3 alone). (FIG. 7E) SiHa, HeLa, HCT-8, HCT 116, MCF-7, and MDA-MB-231 cell lines were transfected with 100 nM scrambled siRNA or HRP-3 siRNA (siHRP-3) and then treated without or with 10 Gy radiation for 48 hours. Data of FACS analysis are expressed as means±SD (* denotes no significance, *p<0.05, and **p<0.05 compared with cells treated with radiation alone).

(FIGS. 8A and 8B) H1299 cells were transfected with 100 nM scrambled siRNA or HRP-3 siRNA (siHRP-3) and then treated without or with 10 Gy radiation for 48 hours. Morphological changes were observed by light microscopy (FIG. 8A, left; scale bar: 1 mm), and apoptosis was determined by FACS analysis (FIG. 8A, right); data are expressed as means±SD (p<0.005 and *p<0.0005 compared with untreated). The levels of HRP-3 and apoptosis-related proteins were detected by Western blotting (FIG. 8B). (FIGS. 8C and 8E) H1299 cells were transfected with 100 nM scrambled siRNA or HRP-3 siRNA (siHRP-3) for 48 hours. The levels of ROS-related proteins (FIG. 8C) and apoptosis-related proteins (FIG. 8E) were determined by Western blotting. (FIG. 8D) H1299 cells were transfected with 100 nM scrambled siRNA or HRP-3 siRNA (siHRP-3) and then treated without or with 10 Gy radiation for 48 hours in the absence or presence of 3 mM NAC. Cells stained with 10 nM DCF-DA were analyzed by a laser-scanning confocal microscope (FIG. 8D, left; scale bar: 1 mm), and ROS production was assessed by FACS analysis with 10 nM DCF-DA (FIG. 8D, right); data are expressed as means±SD (**p<0.05 compared with controls).

(FIG. 9A) H1299 cells were transfected with 100 nM scrambled siRNA or HRP-3 siRNA (siHRP-3) for 48 hours. The levels of HRP-3, IκB, Myc and Noxa proteins were detected by Western blotting (left), and NF-κB transcriptional activity was determined by reporter gene assay (right); data are expressed as means±SD (*p<0.05 compared with controls). (FIGS. 9B-D) H1299 cells were transfected with 100 nM scrambled siRNA or HRP-3 siRNA (siHRP-3) and then left untreated or treated with 10 Gy radiation (FIG. 9B), 3 mM NAC (FIG. 9C), or 2 µM BAY 11-7082 (FIG. 9D) for 48 hours. The levels of HRP-3, IkB, Myc and Noxa proteins were detected by Western blotting (left), and NF-κB transcriptional activity was determined by reporter gene assay; data are expressed as means±SD (*p<0.05 and **p<0.005 compared with untreated controls in FIG. 9B: *p<0.05 compared with cells transfected with siHRP-3 alone in FIG. 9C and FIG. 9D).

DETAILED DESCRIPTION OF THE INVENTION

Figure 1A:
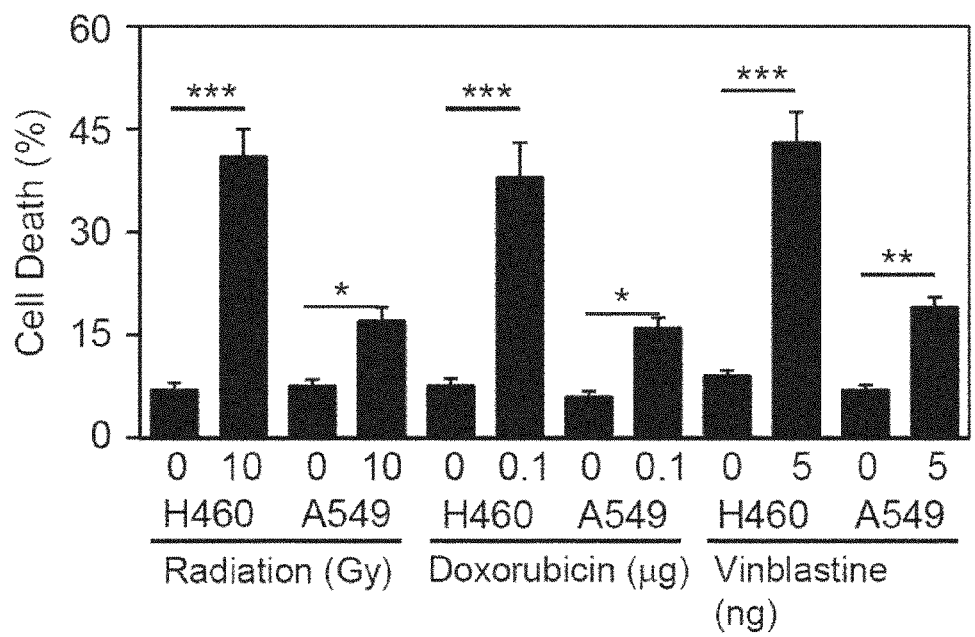
FIGS. 1A-C show a correlation between HRP-3 and the radiation- and drug-resistances of A549 cells.

In one aspect, the present invention provides a pharmaceutical composition for treating radiation- or drug-resistant cancers, including a therapeutic agent capable of inhibiting the expression of HRP-3.

The present inventors have conducted various studies to develop a method capable of more effectively treating cancer patients having radiation- or drug-resistant cancers, and paid attention to HRP-3 during such studies. As a result, the present inventors constructed an siRNA capable of inhibiting the expression of HRP-3, and have found that the siRNA can inhibit the expression of HRP-3 in A549 cells. Then, the present inventors examined changes in the characteristics of A549 cells transfected with HRP-3 siRNA, and as a result, found that the siRNA can reduce the proliferation of A549 cells, reduce colony formation, increase the apoptosis of A549 cells, and enhance the expression of apoptotic markers, and that the intracellular expression level of HRP-3 is temporarily increased by treatment with radiation or anticancer drugs. In addition, the present inventors have found that when A549 cells are transfected with HRP-3 siRNA and treated with radiation or anticancer drugs, the death rate of the A549 cells can be significantly increased, colony formation can be significantly reduced, and the expression of apoptotic markers in the cells can be significantly increased.

Moreover, the expression levels of ROS production-related molecules were compared in order to the mechanism by which HRP-3 siRNA increases the death of cancer cells. This revealed that antioxidant coordinators such as the transcription factor Nrf2 and its target HO-1 are highly expressed in A549 cells that highly express HRP-3, and when the expression of HRP-3 in the A549 cells is inhibited, the levels of the antioxidant coordinators in the cells are reduced and the level of reactive oxygen species (ROS) in the cells is increased, and the inhibition of HRP-3 expression in combination with radiation or anticancer drug treatment, results in a significant increased the level of ROS.

As described above, it was found that the inhibition of HRP-3 expression in cancer cells results in increased the intracellular level of ROS to increase the death rate of the cancer cells. Thus, an examination was performed on whether the inhibition of HRP-3 expression can also influence the level of p53 protein that is activated by ROS. This revealed that the cells, which were inhibited of HRP-3 expression, increased the expression and activation of p53 tumor suppressor protein and also PUMA, a key mediator of p53-dependent apoptosis, and the inhibition of HRP-3 expression in combination with radiation or treatment with anticancer drugs led to a significant increase in levels of p53, pp53, PUMA, etc.

Meanwhile, it was found that the inhibition of HRP-3 expression in cancer cells that express no p53 can induce increased ROS production, leading to increased activity of NF-κB as an upstream signaling of c-Myc and Noxa apoptotic pathway, thereby inducing apoptosis of the cancer cells. In addition, it was found that anticancer effects of inhibition of HRP-3 expression appear not only in lung cancer cells, but also in various cancer cells, including cervical cancer, colorectal cancer, and breast cancer in the same or similar way.

As described above, the inhibition of the expression of HRP-3 protein that causes the radiation resistance and drug-resistance of lung cancer cells such as A549 cells or H1299 cells can lead to increased death rate of A549 cells or H1299 cells and can also show the same or similar effects against cancer cells (cervical cancer, colorectal cancer, and breast cancer cells, etc.) other than lung cancer cells. Thus, when a therapeutic agent capable of inhibiting the expression of HRP-3 is used in combination with radiation or anticancer drugs, it can significantly increase the apoptotic rate of various cancer cells, suggesting that it can be used for the treatment of patients showing resistance to anticancer treatment.

As described above, a therapeutic agent capable of inhibiting the expression of HRP-3 according to the present invention can show the effects of i HRP-3 and inducing reactive oxygen species (ROS)-dependent p53 activation or ROS-dependent NF-κB activation, thereby removing or attenuating the radiation resistance or anticancer drug resistance caused by expression of HRP-3 in cancer cells. The method of the present invention makes it possible to treat cancer using conventional anticancer drugs showing resistance and to remove or attenuate the resistance of cancer cells themselves, thus treating resistant cancer without needing to develop a new anticancer drug. This method was not reported by any research group in the prior art and was first provided by the present inventors. Thus, the pharmaceutical composition according to the present invention may be administered alone to a subject having cancer, but may preferably be administered in combination with radiation or other anticancer compositions (e.g., doxorubicin, vinblastine, etc.).

As used herein, the term "HRP-3" refers to a kind of HRP (hepatoma-derived growth factor (HDGF)-related protein), being a growth factor protein that promotes the proliferation of mammalian fibroblasts, exhibits the effect of stimulating angiogenesis in endothelial cells by VEGF-non-dependent mechanisms and is overexpressed in various tumor cells, including neurocytoma and lung cancer cells. The amino acid sequence of the HRP-3 protein or the polynucleotide sequence of the gene encoding the HRP-3 protein can be obtained from known databases such as NCBI GenBank (e.g., GenBank No. AB029156.1). However, in addition to the known sequence described above, variants resulting from the addition, substitution, or deletion of some amino acid residues in the known amino acid sequence can also fall within the scope of the present invention, as long as they show the effect of causing cancer cell resistance to radiation or anticancer drugs in the same manner as HRP-3.

As used herein, the expression "an agent capable of inhibiting expression" refers to a substance capable of inhibiting the production of a transcript or protein being generated by the expression of a gene. Examples of the agent used in the present invention include transcription factors that bind to genes to silence the genes at the transcriptional level; interfering RNAs, including miRNA, siRNA, and shRNA, which bind to transcripts synthesized by transcription so as to degrade the transcripts; and antibodies capable of binding to expressed HRP-3 protein.

As used herein, the term "interfering RNA (short interfering RNA)" refers to a double-stranded RNA capable of inducing an RNAi that inhibits the activity of genes. The interfering RNA used in the present invention may be an miRNA, an siRNA, an shRNA, or the like, which can inhibit the expression of HRP-3. Further, the interfering RNA may be any interfering RNA that induces HRP-3 mRNA. For example, the interfering RNA may be either an siRNA obtained by chemical synthesis, biochemical synthesis, or in vivo synthesis, or a double-stranded RNA consisting of at least 10 base pairs, which results from in vivo degradation of a double-stranded RNA consisting of at least about 40 bases. Preferably, it may be an siRNA including either a nucleotide sequence consisting of SEQ ID NOS: 5 and 6 or a nucleotide sequence consisting of SEQ ID NOS: 7 and 8.

The interfering RNA may be composed of a sequence having a homology of at least about 70%, preferably at least 75%, more preferably at least 80%, even more preferably at least 85%, even more preferably at least 90%, particularly preferably at least 95%, and most preferably at least 100%, to a portion of the nucleic acid sequence of HRP-3 RNA. In addition, an RNA including the double-stranded portion, or a modification thereof, may also be used in the present invention. The sequence portion having the homology may generally be composed of at least 15 nucleotides, preferably about 19 nucleotides, more preferably at least 20 nucleotides, and even more preferably at least 21 nucleotides.

As used herein, the term "antibody" means a protein molecule that can bind specifically to the antigenic site of a protein or peptide molecule. This antibody can be produced by cloning each gene into an expression vector according to a conventional method to obtain a protein encoded by the marker gene, and producing the antibody from the thus obtained protein according to a conventional method. The antibody used in the present invention is not specifically limited, and examples thereof include polyclonal antibodies, monoclonal antibodies, or fragments thereof that can bind to antigens, all immunoglobulin antibodies, and recombinant antibodies such as humanized antibodies. In addition, the antibody includes not only a complete form having two full-length light-chains and two full-length heavy chains, but also functional fragments of the antibody molecule. As used herein, the expression "functional fragments of the antibody molecule" refers to fragments having at least a function of binding to antigens, such as Fab, F(ab'), F(ab')2, and Fv.

In the present invention, the antibody may be an antibody capable of binding specifically to HRP-3 protein. Preferably, it may be a monoclonal antibody, a polyclonal antibody, or fragments thereof, which can bind specifically to HRP-3 protein.

As used herein, the term "resistant cancer" refers a cancer showing very low sensitivity to treatment with anticancer drugs or radiation so that the symptoms thereof are not improved, relived, alleviated, or treated by the anticancer drug or radiation treatment. The resistant cancer can be a cancer originally resistant to treatment with a specific anticancer drug or radiation. Alternatively, the resistant cancer can be a cancer not originally resistant, but is no longer resistant to a therapeutic drug because a gene in the cancer cells is mutated due to long-term administration of the therapeutic drug.

In the present invention, the resistant cancer may be any cancer showing resistance to radiation or anticancer treatment, but is not specifically limited thereto. Examples of the resistant cancer include lung cancer, cervical cancer, colorectal cancer, breast cancer, etc., showing resistance to radiation or anticancer drug treatment due to overexpression of HRP-3. Herein, the lung cancer may be non-small-cell lung cancer that overexpresses HRP-3, but is not limited thereto.

The inventive pharmaceutical composition for treating a radiation- or drug-resistant cancer includes an HRP-3 inhibitor showing the effects of not only increasing the production of ROS in cancer cells, but also inhibiting the radiation or drug resistance caused by HRP-3. Thus, when the pharmaceutical composition of the present invention is administered alone to a patient having a radiation- or drug-resistant cancer, the radiation- or drug-resistant cancer is treatable. Also, when the pharmaceutical composition of the present invention is administered to a patient in combination with conventional anticancer drugs showing no particular therapeutic effect due to resistance caused by HRP-3, the radiation- or drug-resistant cancers in the patient is treatable. Particularly, when the pharmaceutical composition of the present invention is administered in combination with a conventional anticancer drug, the anticancer activity of the conventional anticancer drug overlaps with the anticancer activity of the pharmaceutical composition of the present invention, thereby more effectively treating cancer. Herein, the conventional anticancer drug used in combination with the pharmaceutical composition of the present invention may be any anticancer drug to which cancer cells can show resistance due to HRP-3. Preferred examples of the conventional anticancer drug include, but are not limited to, doxorubicin, vinblastine, taxol, etoposide, cisplatin, 5-FU, ifosfamide, etc., useble alone or in combination.

Figure 1B:
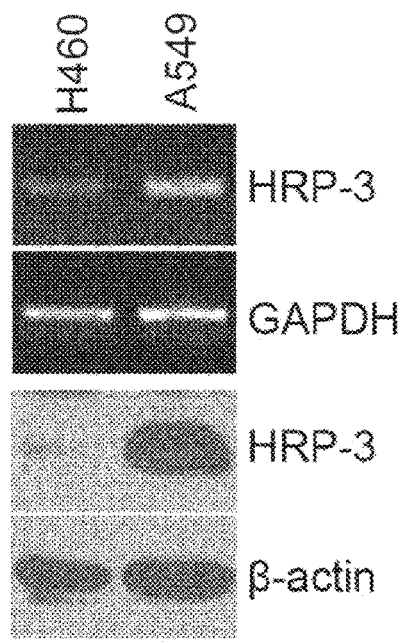

In an embodiment of the present invention, it was shown that A549 cells showed high levels of resistance to radiation and anticancer drugs (doxorubicin and vinblastine) (FIG. 1A), and HRP-3 was highly expressed in the cells (FIG. 1B). Also, HRP-3 was distributed in the nucleus of A549 cells (FIG. 1C), and the inhibition of HRP-3 expression reduced the proliferation of A549 cells in a time-dependent fashion (FIG. 2C), increased the apoptosis of A549 cells (FIG. 2D), increased the levels of cleaved PARP and caspase-3 that are apoptotic markers (FIG. 2E), and also reduced colony formation (FIG. 2F).

Moreover, when A549 cells were treated with an siRNA that inhibits the expression of HRP-3, the apoptosis of the A549 cells could be induced, but when the siRNA was used in combination with radiation, doxorubicin, or vinblastine, the death rate of the A549 cells could be increased (FIG. 3B). In addition, it was found that, when both the inhibition of HRP-3 expression and radiation were applied to A549 cells, colony formation decreased by about 74% compared to A549 cells compared to siHRP-3 alone, and HRP-3-depleted cells were also more sensitive than control cells to exposure to 0 or 6 Gy of radiation (FIGS. 3C and 3D).

Figure 4A:
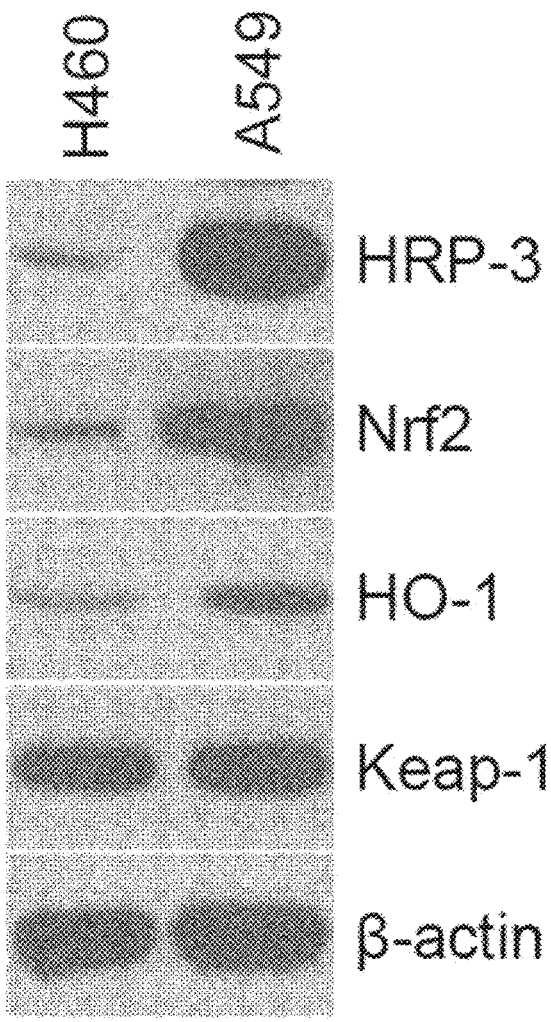
FIGS. 4A-D show that the inhibition of HRP-3 expression during the apoptosis of A549 cells induces ROS generation via inhibition of the Nrf2/HO-1 pathway.
Figure 4B:
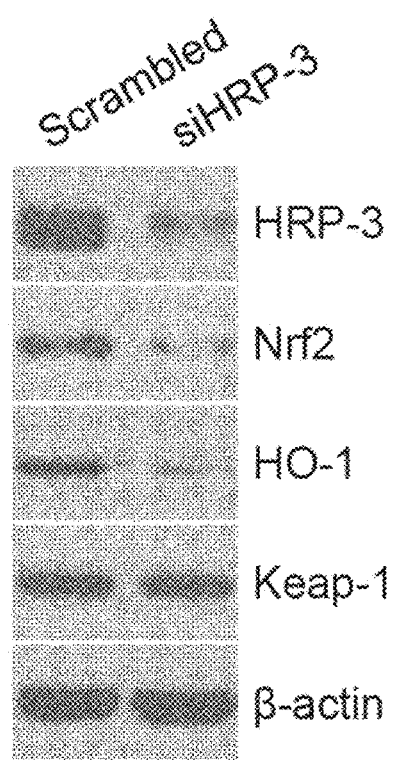
Figure 4C:
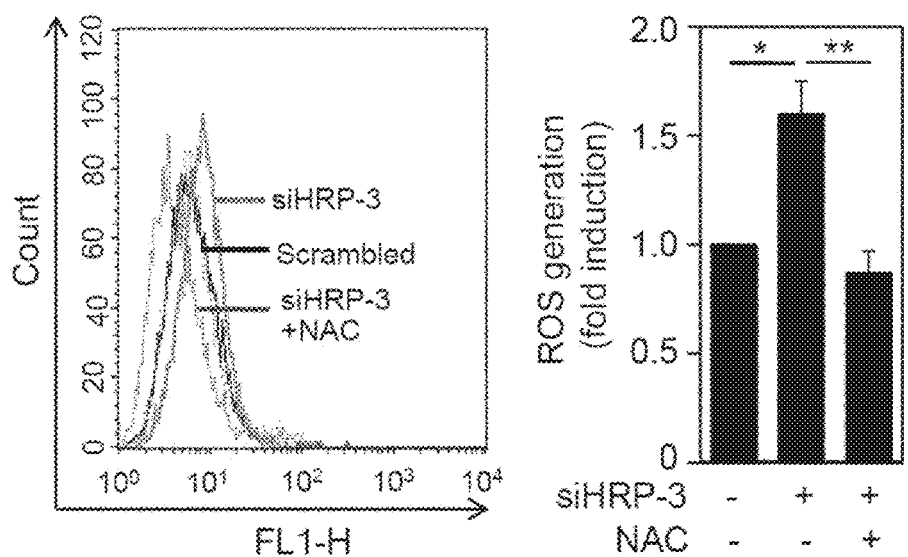
Figure 4D:
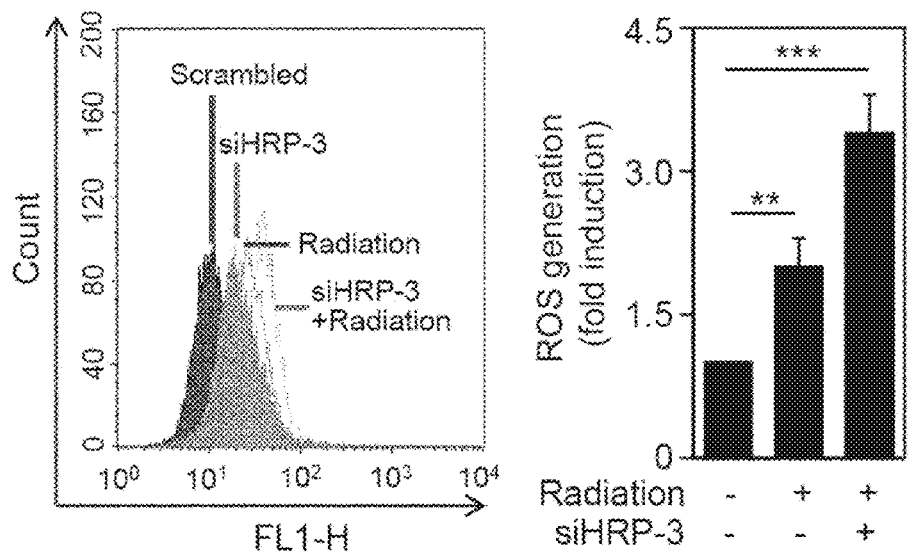

Meanwhile, it was shown that, when A549 cells were treated with an siRNA that inhibits the expression of HRP-3, the levels of antioxidant coordinators such as the transcription factor Nrf2 and its target HO-1, were decreased (FIG. 4B), and the inhibition of HRP-3 expression induced an approximate 1.6-fold increase in ROS generation compared to control cells, which was inhibited by treatment with NAC (FIG. 4C). Also, it was shown that ROS generation in cells subjected to both the inhibition of HRP-3 expression and radiation was significantly increased (FIG. 4D).

Figure 5A:
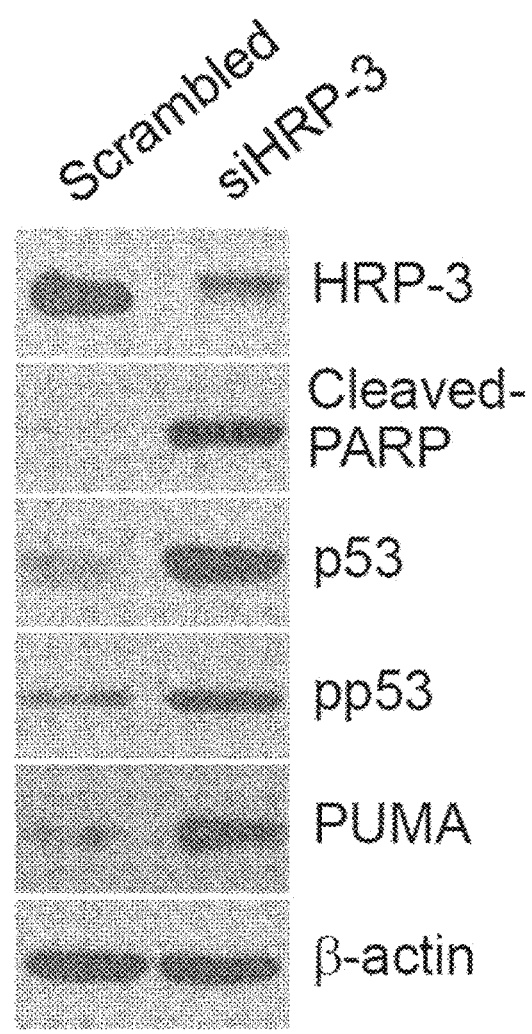
FIGS. 5A-D show that the inhibition of HRP-3 expression promotes ROS-dependent activation of p53 signaling for apoptosis of A549 cells.
Figure 5B:
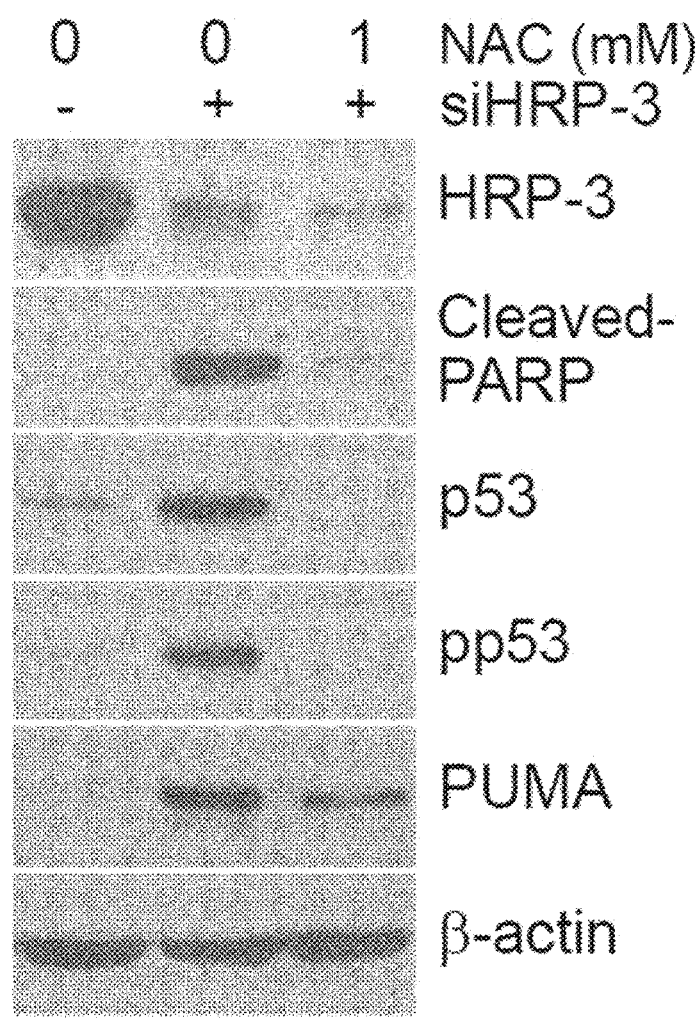
Figure 5C:
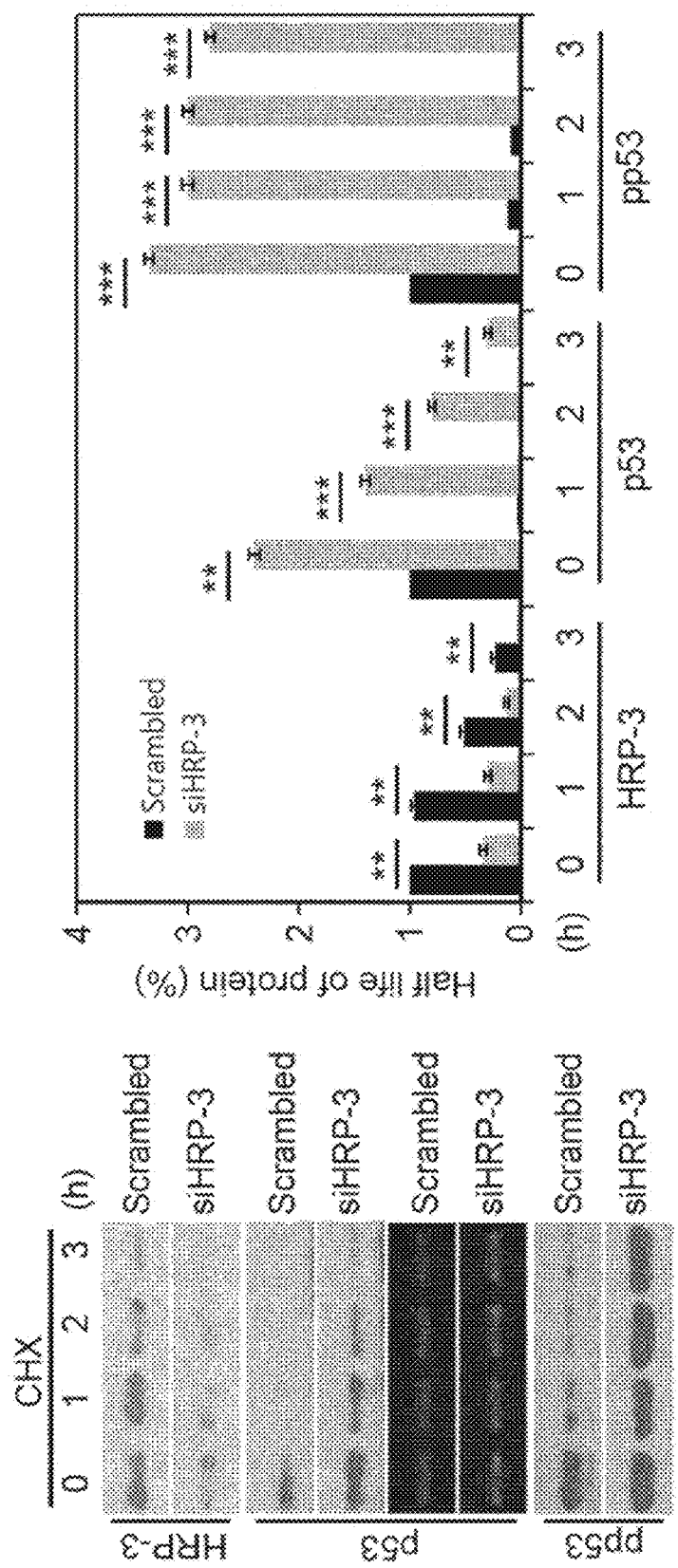
Figure 5D:
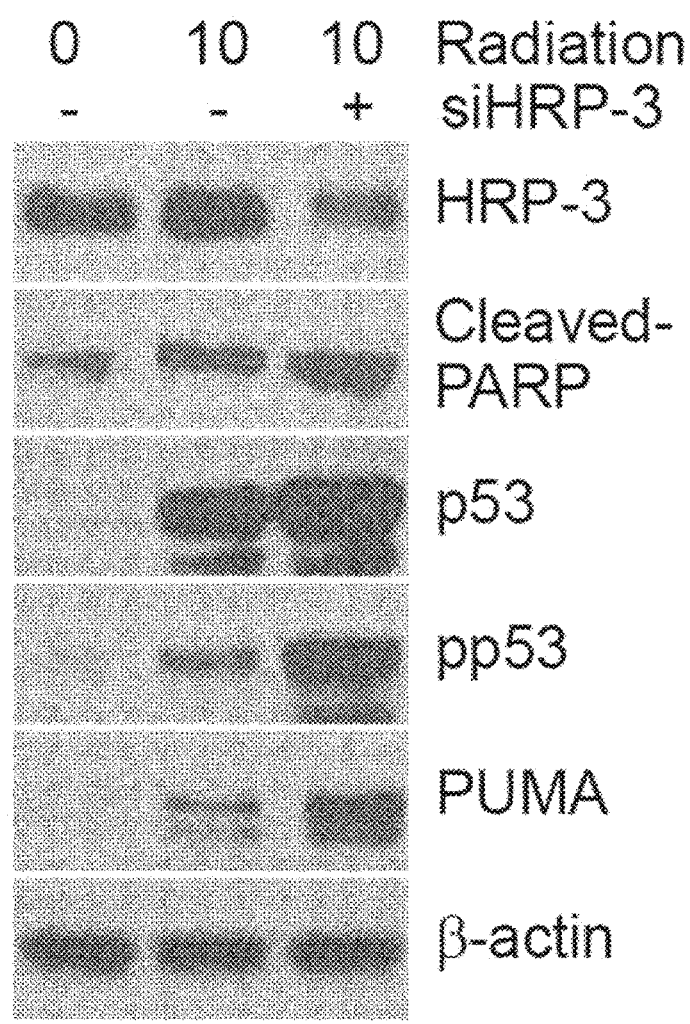

In addition, it was confirmed that transfection of A549 cells with HRP-3-specific siRNA induced the expression and activation of p53, a tumor suppressor protein, and also that of PUMA, a key mediator of p53-dependent apoptosis, compared to controls (FIGS. 5A and 5B), and HRP-3 was involved in regulating p53 activation (FIG. 5C), and during the process of apoptosis, p53 and PUMA were significantly increased in radiation-treated, A549 cells, which were inhibited of HRP-3 expression, compared with control cells or cells treated with radiation alone (FIG. 5D).

The above-described results show that the inhibition of the HRP-3 protein expression that causes radiation-resistance and drug-resistance in A549 cells can increase the apoptosis of A549 cells, and when the inhibition of HRP-3 expression is performed in combination with radiation or anticancer drug treatment, the apoptotic rate of A549 cells can be significantly increased, suggesting that the inhibition of HRP-3 expression can be applied for the treatment of patients showing resistance to anticancer chemotherapy.

Figure 6A:
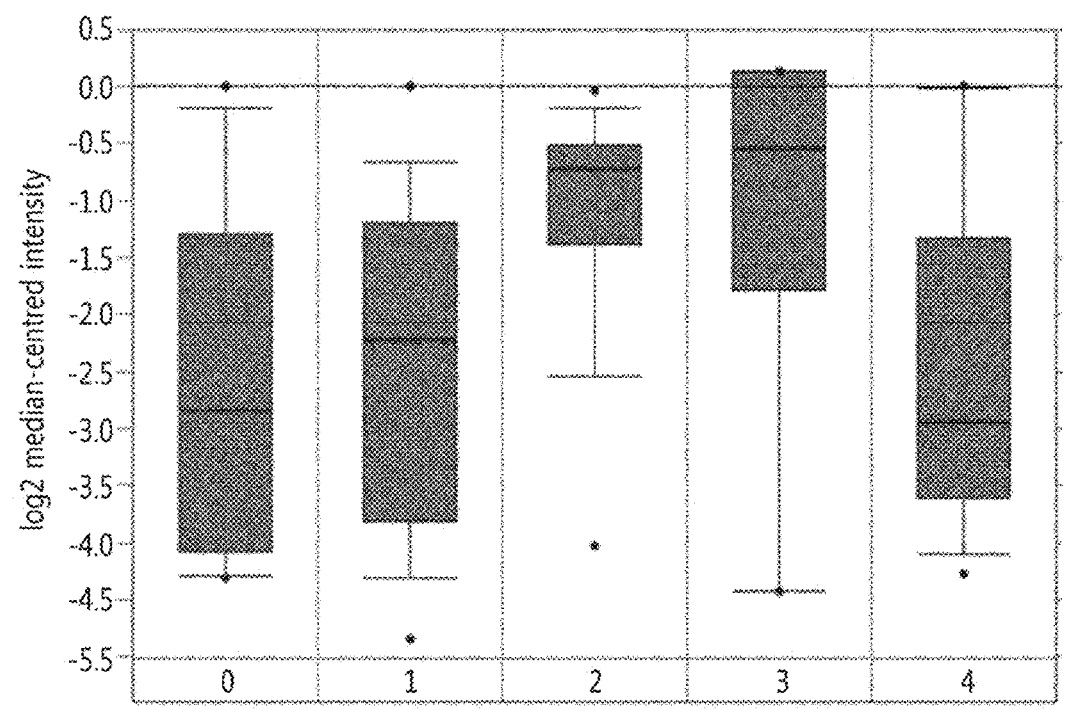
FIGS. 6A-E show that HRP-3 is associated with the resistant phenotype of p53 null-type H1299 cells.
Figure 6B:
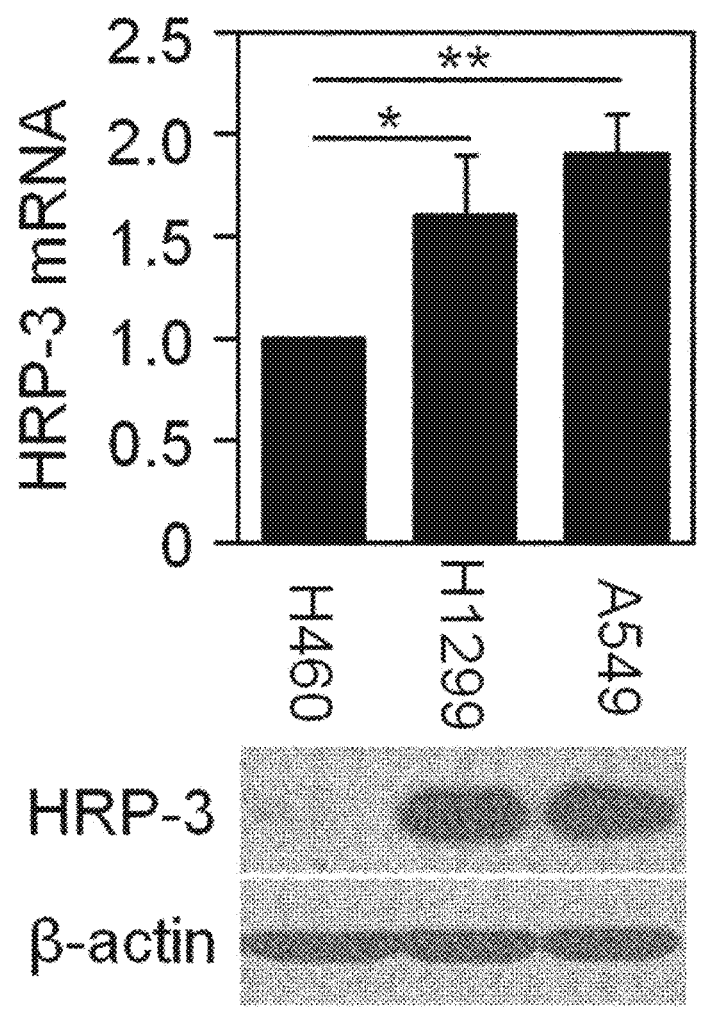

In another embodiment of the present invention, it was confirmed that the expression level of HRP-3 differs between types of lung cancer cells (FIG. 6A), and HRP-3 was highly expressed even in lung cancer lines that express no p53 (FIG. 6B). Also, HRP-3 was localized only in the nucleus of lung cancer cell lines that express no p53 (FIG. 6C), and HRP-3 showed a direct response to radiation or anticancer drug treatment (FIG. 6D), and HRP-3 was also localized only in the nuclei of radiation-treated lung cancer cell lines that express no p53 (FIG. 6E).

Figure 7A:
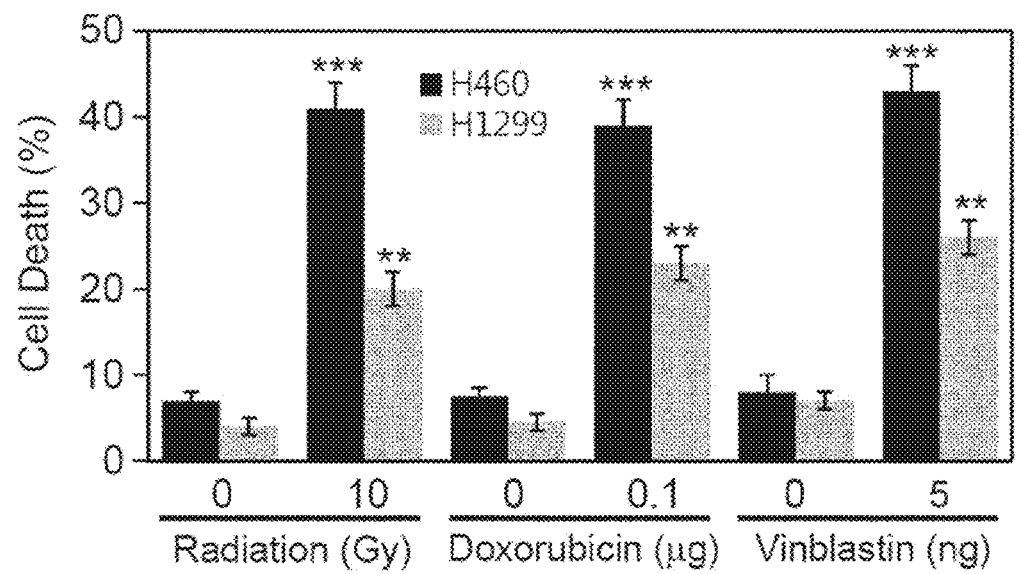
FIGS. 7A-E show the synergistic effect of HRP-3 depletion on cytotoxicity of H1299 cells treated with radiation or anti-cancer drugs.
Figure 7B:
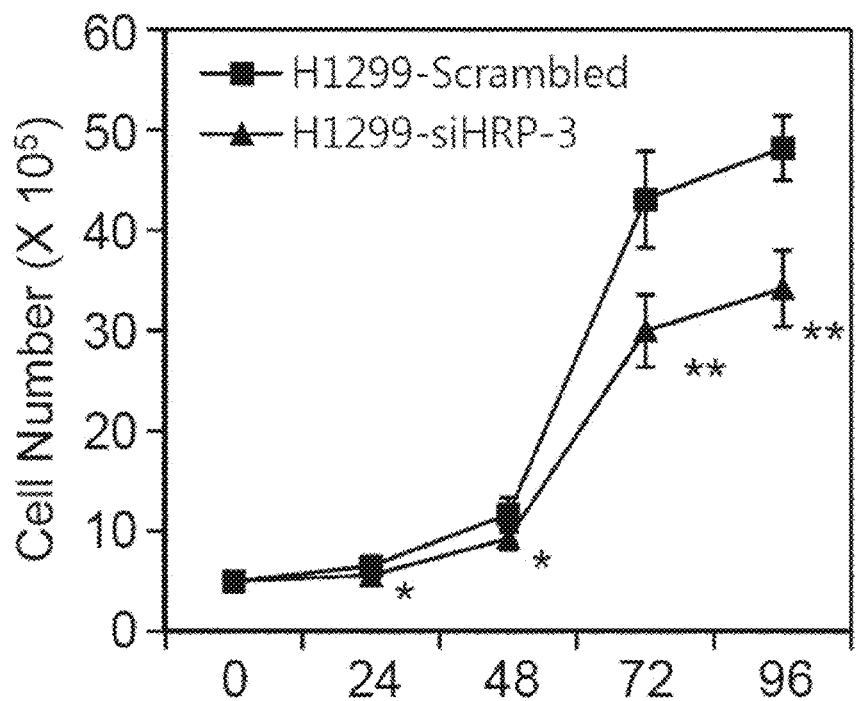

Moreover, it was confirmed that H1299 cells that does not express p53 showed a more significant resistance to anticancer drugs compared to H460 cells, and HRP-3 played an essential role in the survival of H1299 cells (FIG. 7B). Furthermore, it was confirmed that the inhibition of HRP-3 expression in H1299 cells could induce the death of the H1299 cells (FIG. 7C), and the inhibition of HRP-3 expression during the treatment of H1299 cells with anticancer drugs showed a synergistic effect (FIG. 7D), and the inhibition of HRP-3 expression also showed different anticancer effects, depending on the type of cancer cells (FIG. 7E).

Figure 8A:
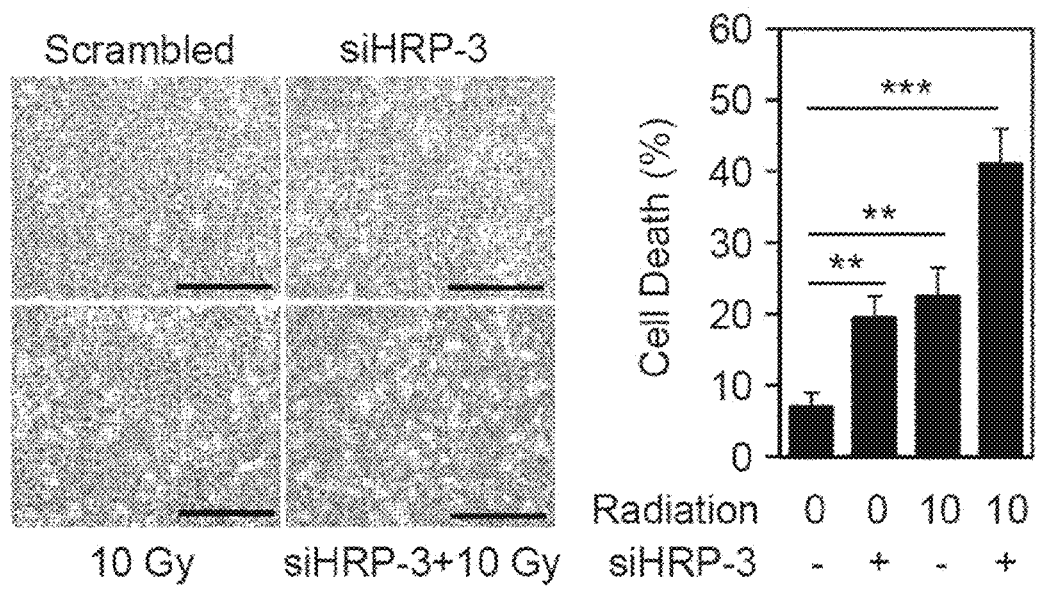
FIGS. 8A-E show that HRP-3 depletion-induced apoptosis is associated with ROS generation, but not Bax family modulation in H1299 cells.
Figure 8B:
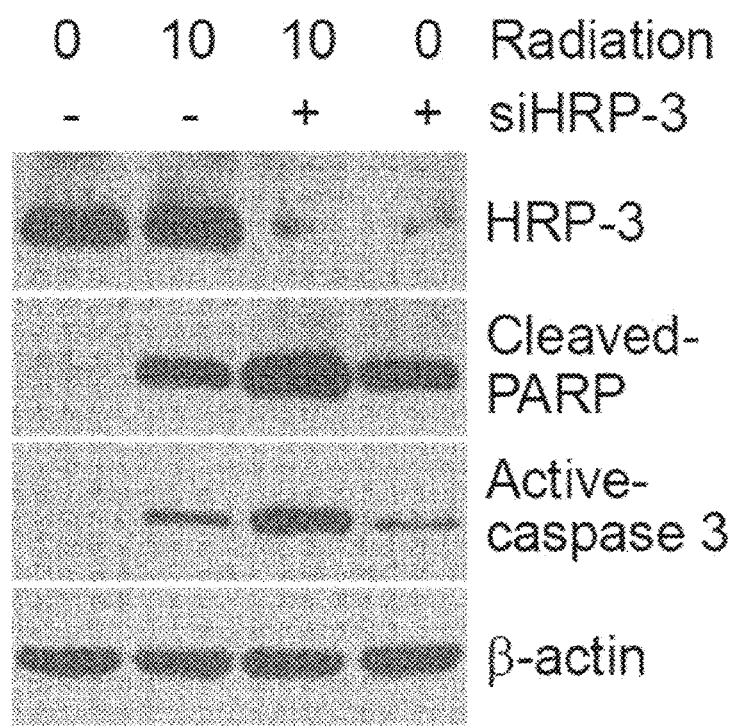

Meanwhile, it was found that, when both the inhibition of HRP-3 expression and radiation were performed, the apoptosis of H1299 cells was further increased (FIG. 8A). Also, it was shown that the levels of cleaved-PARP and active caspase-3, known as apoptotic markers, increased in H1299 subjected to the inhibition of HRP-3 expression or radiation treatment alone, and were the highest in H1299 cells subjected to both the inhibition of HRP-3 expression and radiation treatment (FIG. 8B). Furthermore, it was shown that, in H1299 cells where the expression of HRP-3 was inhibited, the levels of Nrf2 and HO-1 proteins significantly decreased, even though the expression level of the Nrf2 inhibitor Keap-1 in the cells was not changed (FIG. 8C), and in H1299 cells subjected to both the inhibition of HRP-3 expression and radiation treatment, the production of ROS significantly increased, but the production of ROS decreased to the level of control cells by treatment with NAC (FIG. 8D). In addition, it was found that the inhibition of HRP-3 expression in H1299 cells had no association with p53 signaling-related proteins and Bcl-2 family proteins (FIG. 8E).

Figure 9A:
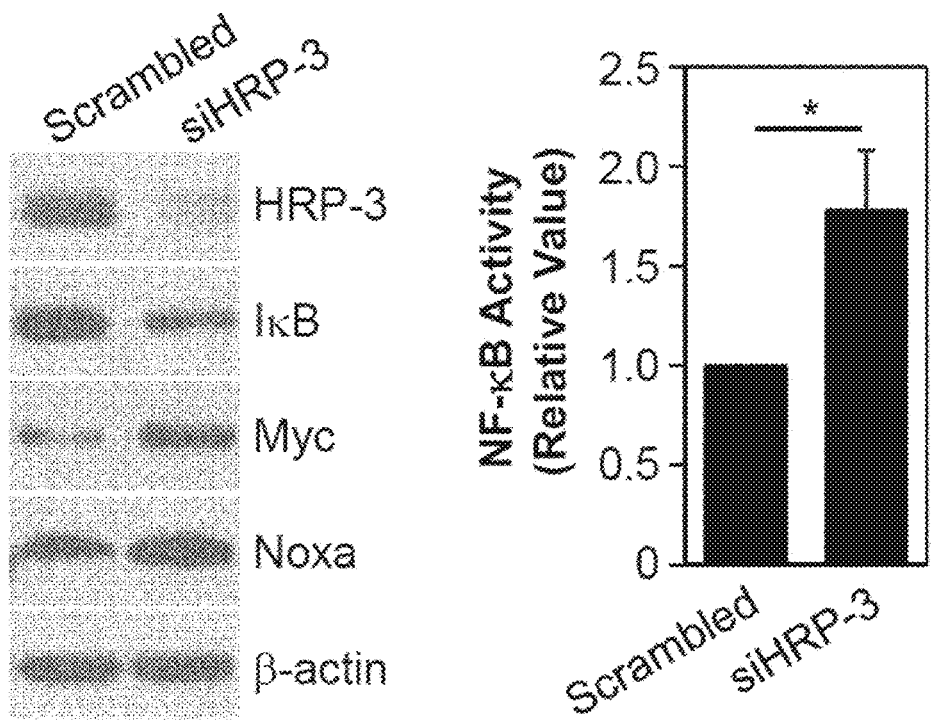
FIGS. 9A-D show that ROS-dependent NF-κB activation and subsequent Myc/Noxa expressions are involved in the apoptosis of HRP-3-depleted H1299 cells.
Figure 9B:
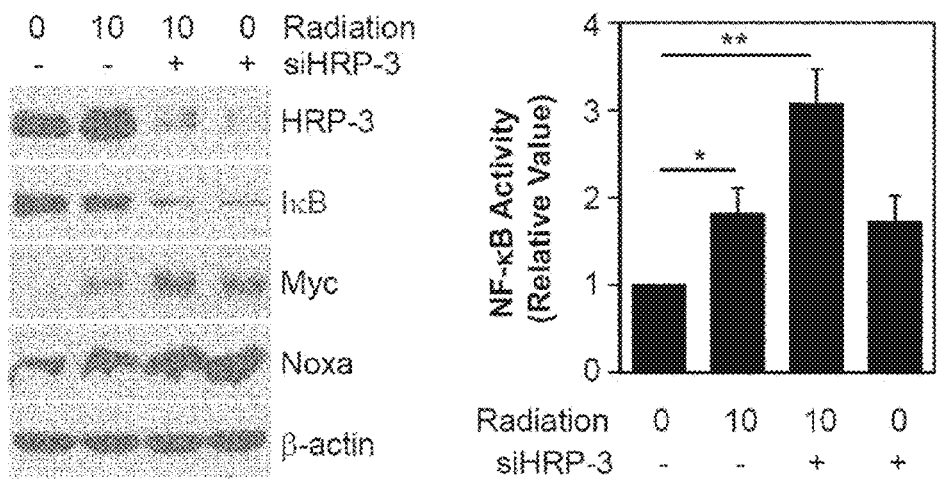
Figure 9C:
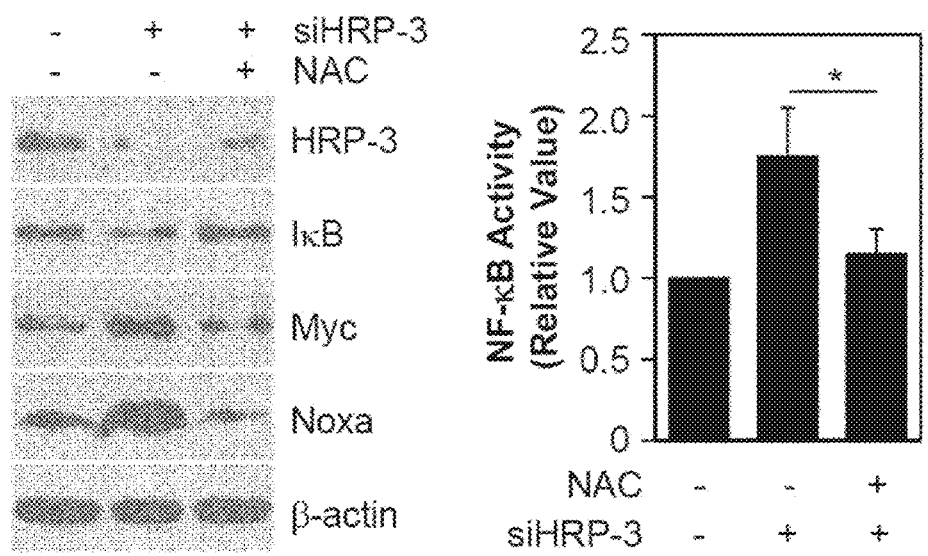
Figure 9D:
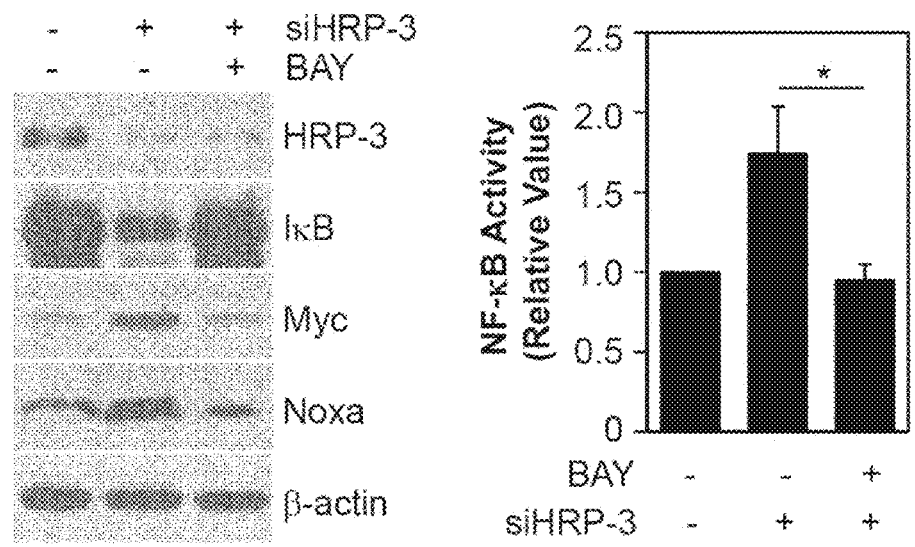

Additionally, it was confirmed that the inhibition of HRP-3 expression in H1299 cells decreased the expression level of IκB, but increased the expression levels of c-Myc and Noxa, and increased NF-κB activity (FIG. 9A). Also, it was confirmed that, when the inhibition of HRP-3 expression in H1299 cells was performed, the expression level of IκB decreased regardless of the presence or absence of radiation, whereas the expression levels of c-Myc and Noxa were increased by the inhibition of HRP-3 expression and radiation treatment, and were the highest when both the inhibition of HRP-3 expression and radiation treatment were performed (FIG. 9B). Furthermore, it was confirmed that, when the inhibition of HRP-3 expression in H1299 cells was performed, the expression level of IκB decreased, but the expression levels of c-Myc and Noxa increased and NF-κB activity increased. It was also confirmed that, when H1299 cells were subjected to both the inhibition of HRP-3 expression and inhibition of ROS production simultaneously, the decrease in the expression level of IκB, the increase in the expression of c-Myc and Noxa, and the increase in NF-κB activity in the cells by the HRP-3 expression were inhibited to levels similar to those of control cells (FIG. 9C). In addition, it was confirmed that, when H1299 cells was subjected to the inhibition of HRP-3 expression, the expression level of IκB decreased, but the expression levels of c-Myc and Noxa increased and NF-κB activity also increased. Additionally, it was confirmed that, when H1299 cells was subjected to both the inhibition of HRP-3 expression and inhibition of NF-κB activity, the decrease in the expression level of IκB, the increase in the expression levels of c-Myc and Noxa, and the increase in NF-κB activity in the cells by the HRP-3 expression were inhibited were inhibited to levels similar to those of control cells (FIG. 9D).

The above-described results show that the inhibition of HRP-3 expression in cancer cells that does not express p53 can induce an increase in ROS production, leading to an increase in NF-κB activity, which activates downstream c-Myc and Noxa signaling pathways, thereby inducing apoptosis of the cancer cells.

The pharmaceutical composition of the present invention may further contain a suitable carrier, an excipient, or a diluent commonly used in the preparation of pharmaceutical compositions. Specifically, the pharmaceutical composition may be formulated conventionally in oral dosage forms, including powders, granules, tablets, capsules, suspensions, emulsions, syrup, and aerosol, preparations for external application, suppositories, and sterile injectable solutions. Carriers, excipients, and diluents possibly contained in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate, mineral oil, etc. The pharmaceutical composition of the present invention may be formulated with commonly-used diluents or excipients, such as fillers, extenders, binders, wetting agents, disintegrants, surfactants, etc. Solid formulations for oral administration may include tablets, pills, powders, granules, capsules, etc., and the solid formulations may include, in addition to the composition, at least one excipient, for example, starch, calcium carbonate, sucrose, lactose or gelatin. In addition to simple excipients, lubricants such as magnesium stearate or talc may also be used. Liquid formulations for oral administration may include suspensions, solutions, emulsions, and syrups, and may contain various excipients, for example, wetting agents, flavoring agents, aromatics, and preservatives, in addition to water and liquid paraffin, which are frequently-used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, etc., may be used. As the base of the suppositories, witepsol, Macrogol, Tween 61, cacao butter, laurin fat, glycerogelatin, etc., may be used.

In an embodiment of the present invention, the content of the agent in the pharmaceutical composition of the present invention may be 0.0001-50 wt %, and preferably 0.01-10 wt %, based on the total weight of the composition, but is not limited thereto.

The pharmaceutical composition of the present invention may be administered in a pharmaceutically effective amount. As used herein, the term "pharmaceutically effective amount" refers to an amount sufficient to treat diseases, at a reasonable benefit/risk ratio applicable to any medical treatment. The effective dosage level of the composition of the present invention may be determined depending on the type of subject, the disease severity, the subject's age and sex, the type of infected virus, the activity of the drug, sensitivity to the drug, the time of administration, the route of administration, excretion rate, the duration of treatment, drugs used in combination with the composition, and other factors known in the medical field. The pharmaceutical composition of the present invention may be administered individually or in combination with other therapeutic agents, and may be administered sequentially or simultaneously with conventional therapeutic agents. The composition can be administered in single- or multiple-dosage form. It is important to administer the composition in the minimum amount that can exhibit the maximum effect without causing side effects, in view of all the above-described factors.

The dosage of the pharmaceutical composition of the present invention can be determined by those skilled in the art depending on the intended use, the severity of the disease, the patient's age, weight, sex, anamnesis, or the kind active ingredient used. For example, the pharmaceutical composition of the present invention may be administered to mammals, including humans, in a daily dosage of 10-100 mg/kg, and preferably 10-30 mg/kg. Also, the composition of the present invention may be administered 1-3 times a day or administered in several divided doses, but is not limited thereto.

In another aspect, the present invention provides a method for treating radiation- or drug-resistant cancer, the method including administering a pharmaceutically effective amount of the pharmaceutical composition of the present invention to a subject having radiation- or drug-resistant cancer. Herein, the pharmaceutical composition may be administered alone to a subject or administered in combination with radiation treatment. Alternatively, the pharmaceutical composition may also be administered in combination with other anticancer compositions (e.g., doxorubicin, vinblastine, etc.).

As used herein, the term "subject" means all animals, including humans, which have the resistant cancer. The resistant cancer is treatable by administering the composition of the present invention to the subject.

As used herein, the term □treatment□ refers to all actions that alleviate or beneficially change radiation- or drug-resistant cancers by administering the pharmaceutical composition of the present invention.

As used herein, the term "administration" means introducing the pharmaceutical composition of the present invention into a subject by any suitable method. The pharmaceutical composition of the present invention may be administered by various oral or parenteral routes, as long as it can reach a target tissue.

In the inventive method for treating the resistant cancer, the pharmaceutical composition of the present invention may be administered by any general route, as long as it can reach a target tissue. The pharmaceutical composition of the present invention may be administered intraperitoneally, intravenously, intramuscularly, subcutaneously, intradermally, orally, intranasally, intrapulmonarily, or intrarectally depending on the intended use, but is not specifically limited thereto.

In still another aspect, the present invention provides the use of a therapeutic agent capable of inhibiting the expression of HRP-3, for preparation of a formulation for a treating radiation- or drug-resistant cancer.

As described above, the present inventors have first found that, when a therapeutic agent capable of inhibiting the expression of HRP-3 is administered to HRP-3-overexpressed cancer cells while the cells are subjected to anticancer treatment, radiation- or drug-resistant cancers can be effectively treated, suggesting that the agent for inhibiting the expression of HRP-3 can be used as an active ingredient in the preparation of a formulation for treating radiation- or drug-resistant cancers. A diluent, excipient, or carrier used in the preparation of the formulation is as described above, and the content of the agent, capable of inhibiting the expression of HRP-3, in the formulation, is also as described above. In addition, the formulation can be prepared using any method known in the art.

MODE FOR THE INVENTION

Hereinafter, the present invention will be described in further detail with reference to examples. It is to be understood, however, that these examples are for illustrative purposes only and are not intended to limit the scope of the present invention.

Example 1

Analysis of Effects of HRP-3 on Apoptosis

Example 1-1

Analysis of Resistance of NSCLC Cell Lines to Radiation and Drug Treatment Human NSCLC cell lines (A549 and H460) were purchased from the ATCC and cultured in RPMI-1640 medium containing 10% FBS, 50 µg/ml streptomycin, and 50 units/ml penicillin. The cultured cells were irradiated using a $^{137}Cs$-ray source (Atomic Energy of Canada, Ltd., Canada) at a dose rate of 3.81 Gy/min and were treated with 0.1 µg/ml doxorubicin or 5 ng/ml vinblastine. The treated cells were treated with trypsin, washed with PBS, stained with annexin V and propidium iodide, and then analyzed by FACS using a flow cytometer to measure apoptosis (FIG. 1A). As shown in FIG. 1A, A549 cells that are NSCLC cells showed higher levels of resistance to radiation and anticancer drugs (doxorubicin and vinblastine) compared to H460 cells.

Example 1-2

Analysis of HRP-3 in NSCLC Cell Line

The phenotype of cells is determined by the genotype. Thus, lung cancer EST libraries (#1611) were analyzed to screen radiation-resistance-related genes, and HRP-3 gene as a radiation-responsive gene was identified using in silico/in vitro analysis of H460 cells. Next, HRP-3 and the control GAPDH (glyceraldehyde-3-phophate dehydrogenase) were subjected to RT-PCR using the following conditions and primers (FIG. 1B):

```
HRP-3 (426 bp; annealing temperature: 58° C.;
28 cycles);

HRP-3 F:
                                    (SEQ ID NO: 1)
5'-ATGAAGGGCTACCCGCACTG-3';

HRP-3 R:
                                    (SEQ ID NO: 2)
5'-CCGGGACTGTTTAGAGGATTTC-3';

GAPDH (305 bp; annealing temperature: 55° C.;
24 cycles);

GAPDH F:
                                    (SEQ ID NO: 3)
5'-CATCTCTGCCCCCTCTGCTGA-3';

GAPDH F:
                                    (SEQ ID NO: 4)
5'-GGATGACCTTGCCCACAGCCT-3'.
```

As shown in FIG. 1B, the expression (top of FIG. 1B) and protein (bottom of FIG. 1B) levels of HRP-3 were higher in A549 cells than in H460 cells.

Example 1-3

Analysis of Intracellular Localization of HRP-3

Each type of human NSCLC cell lines (A549 and H460) was fixed using PBS containing 3.5% formalin at room temperature for 10 minutes. Next, the cells were incubated with 10 µg/ml of rabbit polyclonal anti-HRP-3 antibody (Proteintech Group, Inc.) for 1 hour, and then incubated with fluorescein isothiocyanate-conjugated secondary antibody (Invitrogen, USA). Then, the nucleus of the cells was stained with DAPI (4,6-diamidino-2-phenylindole) (FIG. 1C).

Figure 1C:
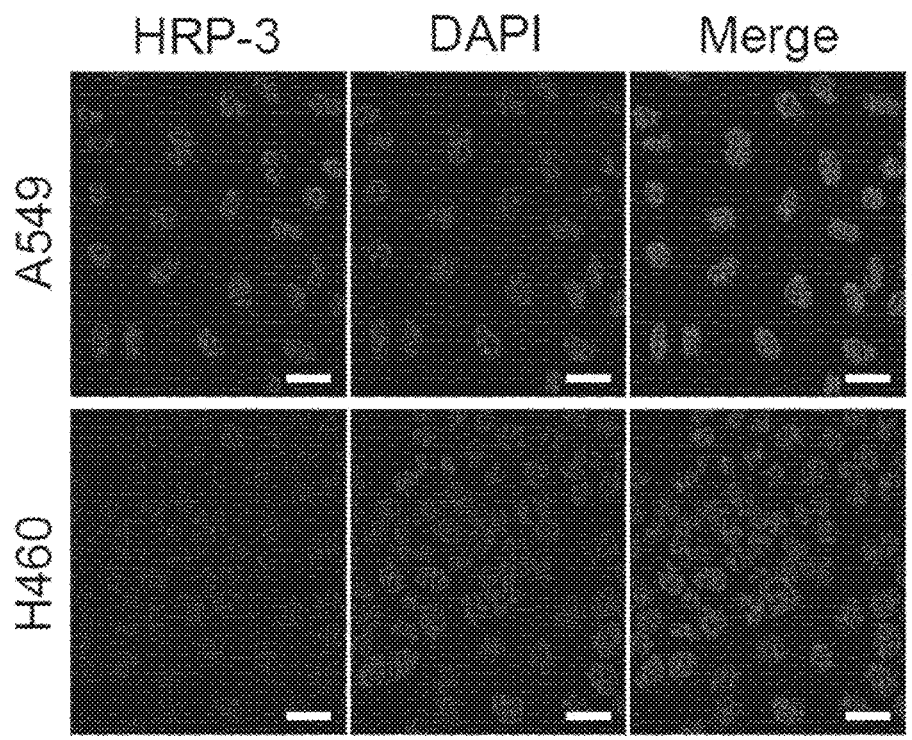

As shown in FIG. 1C, the results of immunofluorescence staining indicated that HRP-3 expression was consistent with the results of Western blotting and that the protein was distributed in the nucleus of A549 and H460 cells.

Example 1-4

Inhibition of HRP-3 Expression

In order to examine whether HRP-3 acts as an important factor in maintaining the resistance of A549 cells, the expression of endogenous HRP-3 in A549 cells was inhibited using siRNAs.

Specifically, siRNA #1 and siRNA #2 were synthesized. Herein, a scrambled siRNA including a polynucleotide without significant homology to a known gene sequence was used as a negative control.

```
HRP-3 siRNA #1;
HRP-3 siRNA #1 F:
                                    (SEQ ID NO: 5)
5'-CCAGUGAAGGGACCUAACUUU-3';

HRP-3 siRNA #1 R:
                                    (SEQ ID NO: 6)
5'-AGUUAGGUCCCUUCACUGGUU-3';

HRP-3 siRNA #2;
HRP-3 siRNA #2 F:
                                    (SEQ ID NO: 7)
5'-GGCCAUGUGUAAAGUUUAAUU-3';

HRP-3 siRNA #2 R:
                                    (SEQ ID NO: 8)
5'-UUAAACUUUACACAUGGCCUU-3'.
```

Figure 2A:
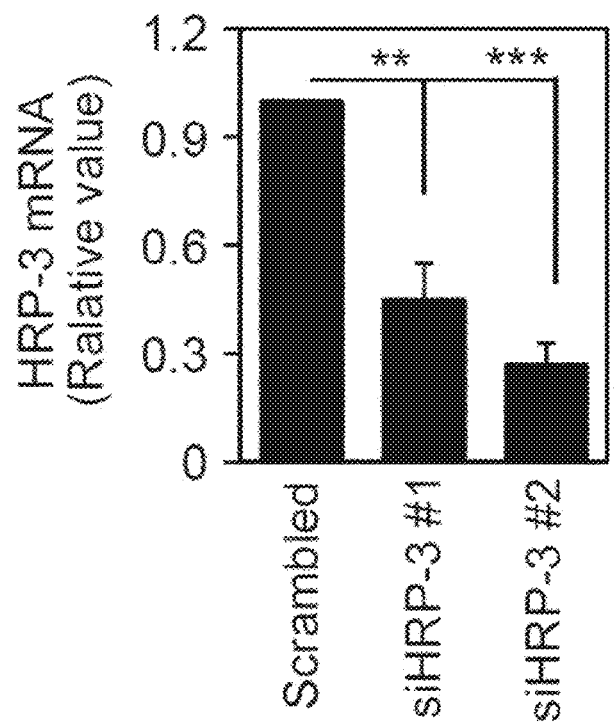
FIGS. 2A-F show that the inhibition of HRP-3 expression in wild-type A549 cells induces apoptosis.
Figure 2B:
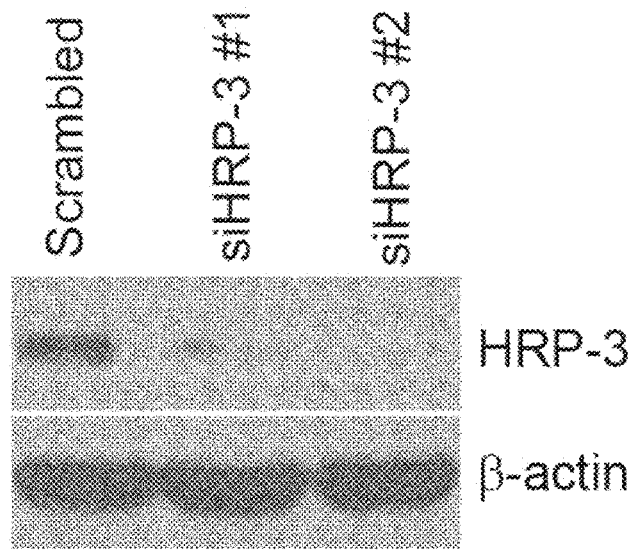

Next, qRT-PCR (quantitative real-time PCR) was performed using chromo 4 cycler and SYBR Premix Ex Taq™, and Western blot analysis was performed using an anti-HRP-3 antibody (Proteintech Group, Inc., USA), and β-actin was used as a loading control (FIGS. 2A and 2B).

As shown in FIGS. 2A and 2B, the results of qRT-PCR (FIG. 2A) and Western blot analysis (FIG. 2B) confirmed that the two siRNAs caused the decrease of HRP-3 expression.

Figure 2C:
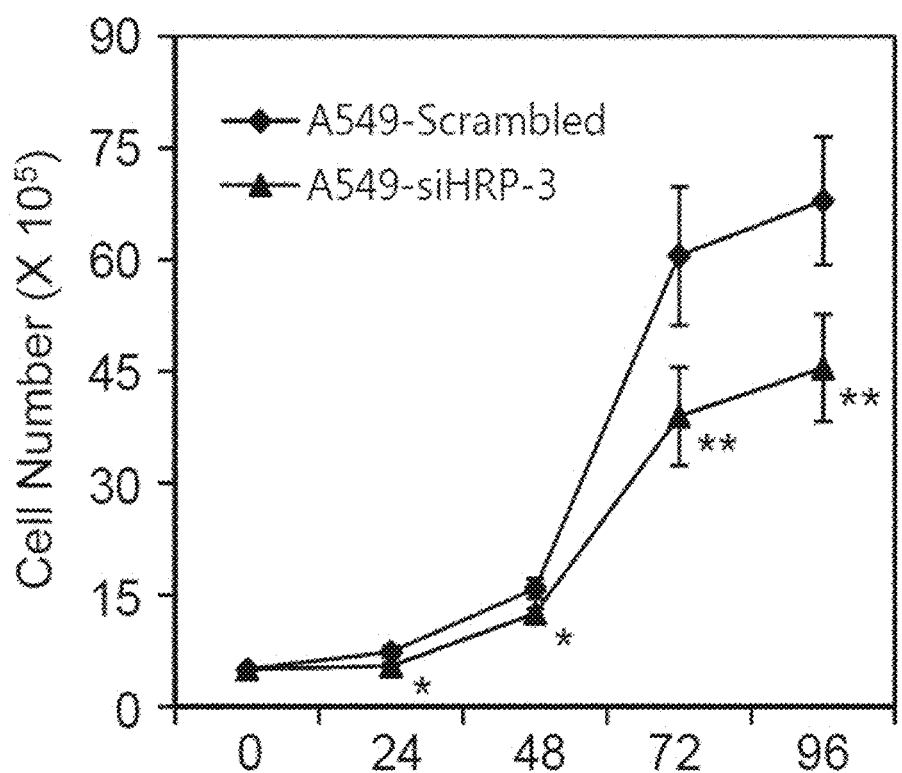

Meanwhile, A549 cells were 100 nM scrambled siRNA or HRP-3 siRNA and cultured for 4 days, and then the proliferation of the cells was determined by cell counting (FIG. 2C).

As shown in FIG. 2C, the inhibition of HRP-3 expression reduced the proliferation of A549 cells in a time-dependent fashion.

Figure 2D:
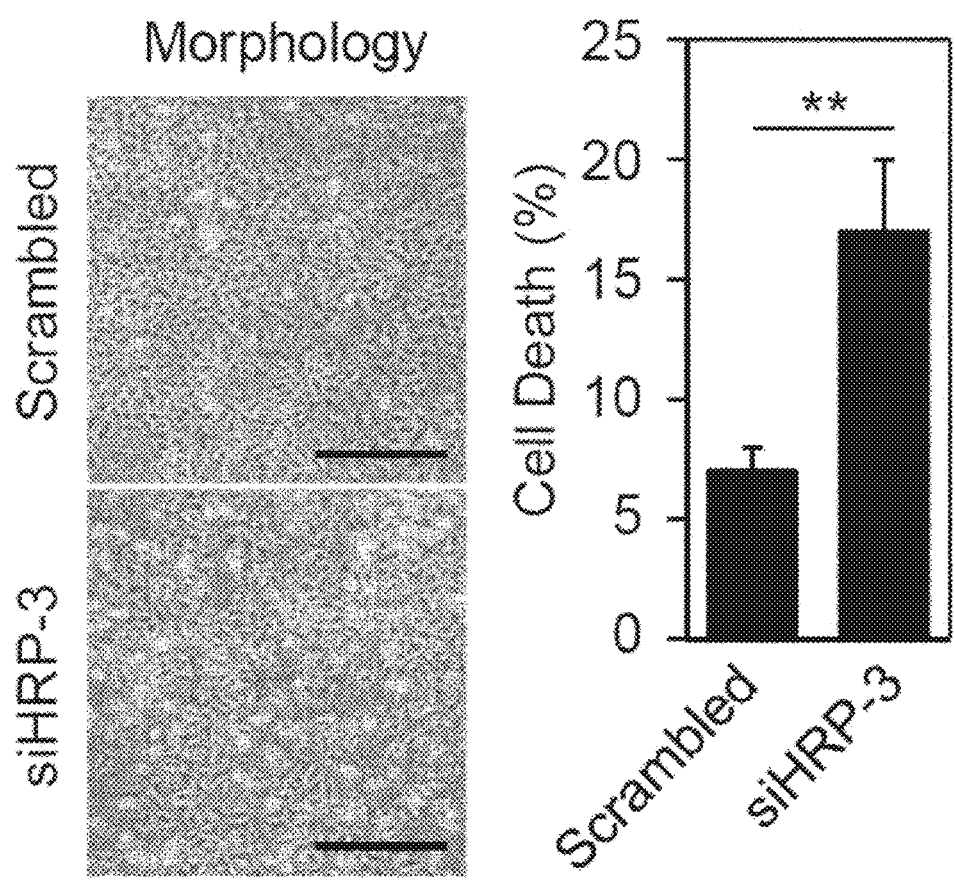
Figure 2E:
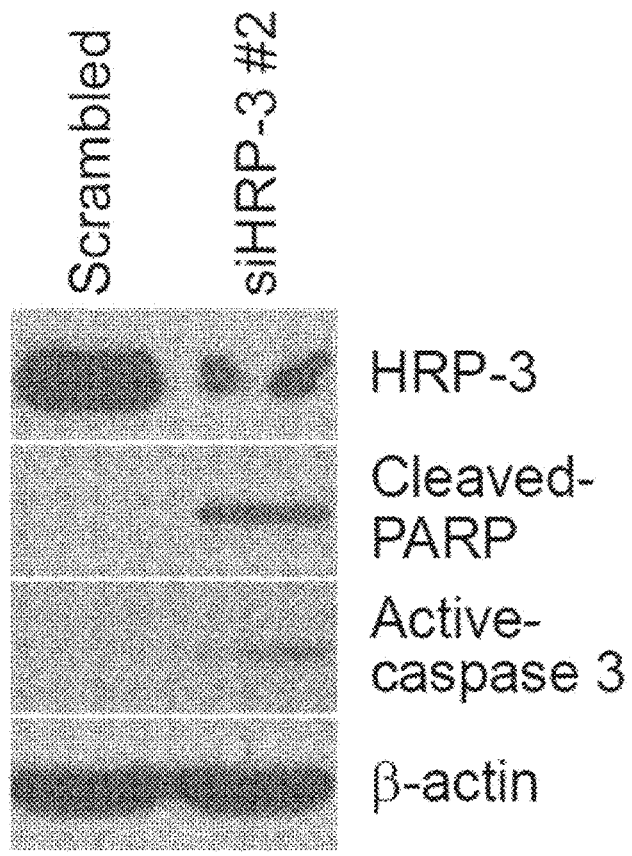
Figure 2F:
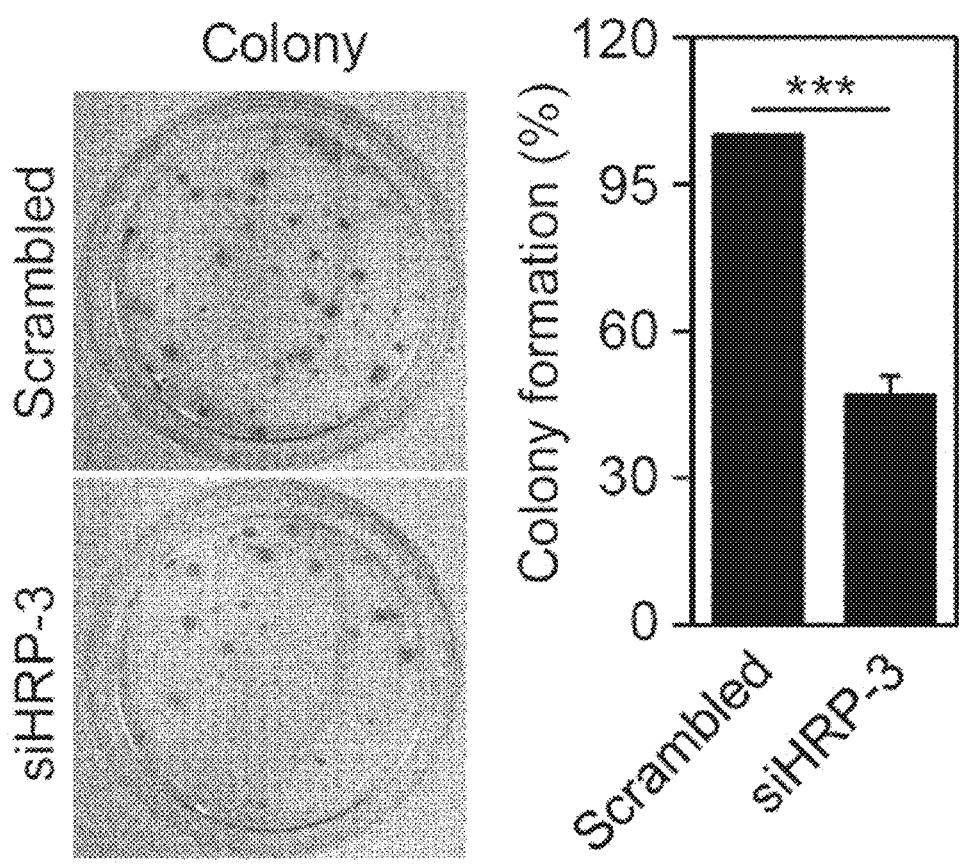

In addition, A549 cells were transfected with 100 nM scrambled siRNA or HRP-3 siRNA and cultured for 2 days. Then, changes in the morphology of the cells were observed under an optical microscope, and the death rate of the cells was measured by FACS analysis (FIG. 2D). Also, the levels of two apoptotic markers (cleaved PARP and active caspase-3) were determined by Western blotting (FIG. 2E).

As shown in FIG. 2D, transfection with HRP-3 siRNA showed an apoptotic rate of about 17%. Also, As shown in FIG. 2E, the levels of the apoptotic markers (cleaved PARP and active caspase-3) increased.

Next, A549 cells were transfected with 100 nM scrambled siRNA or HRP-3 siRNA and cultured for 14 days, and then a colony formation assay was performed. Colonies were fixed with methanol and stained with trypan blue, and colonies exceeding 50 cells were counted using a colony counter (Imaging Products, USA) (FIG. 2F).

As shown in FIG. 2F, the cells, which were inhibited of HRP-3 expression, showed a decrease in colony formation of about 53% compared to the control cells.

Based on the above results, it was confirmed that HRP-3 is essential for maintaining the radiation- and drug-resistant phenotypes of A549 cells.

Example 2

Effect of HRP-3 on Radiation or Anticancer Drug Treatment

Figure 3A:
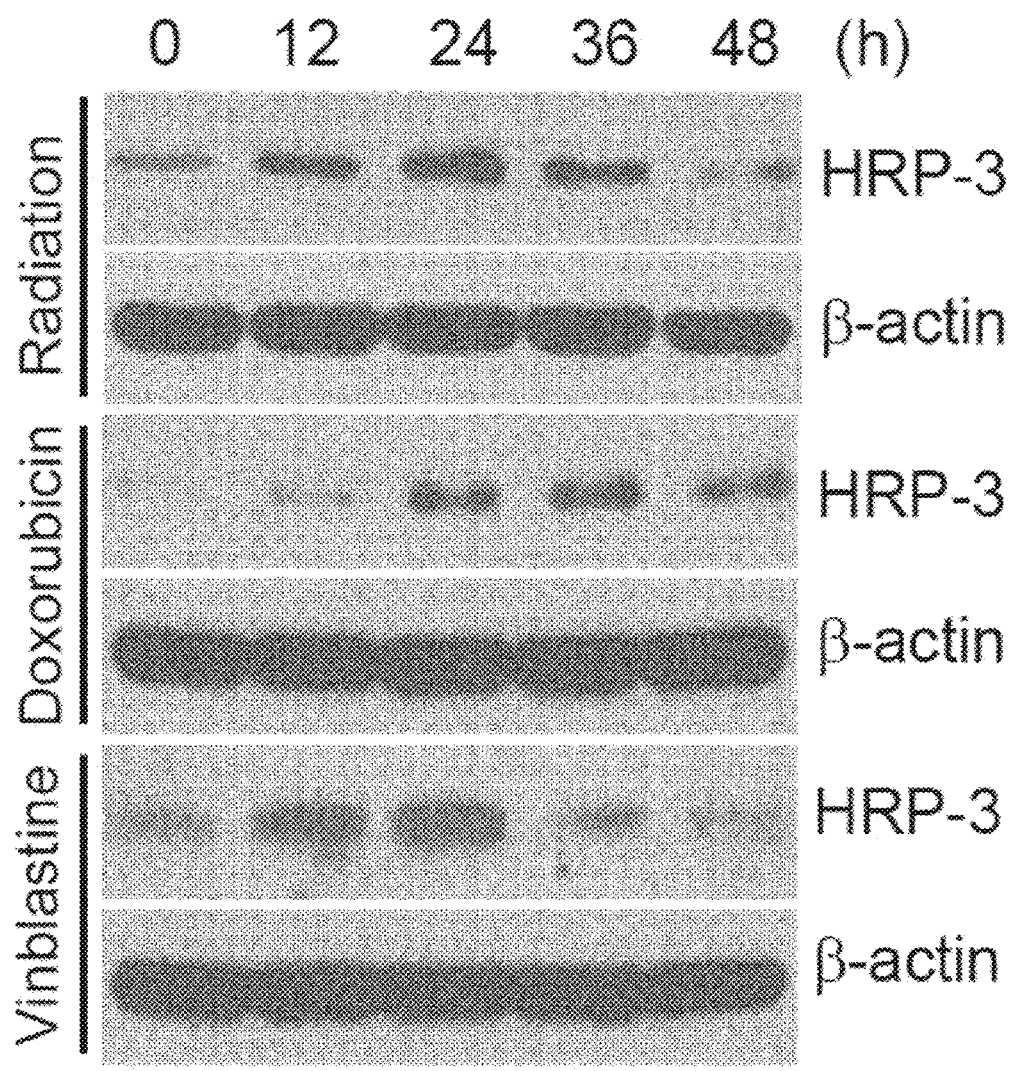
Figure 3C:
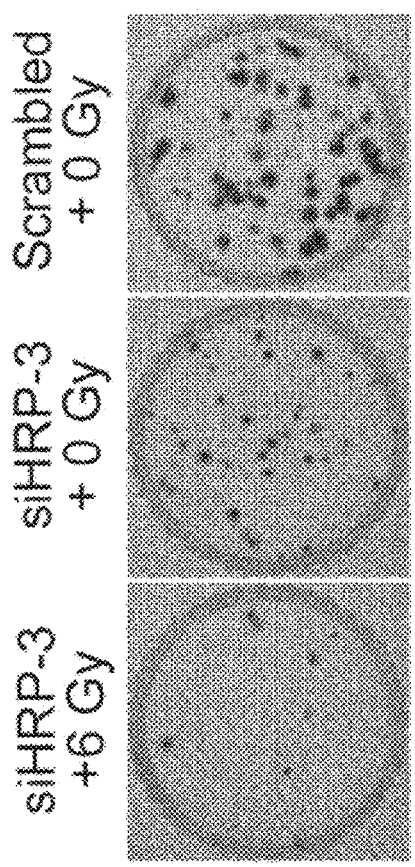
Figure 3C:
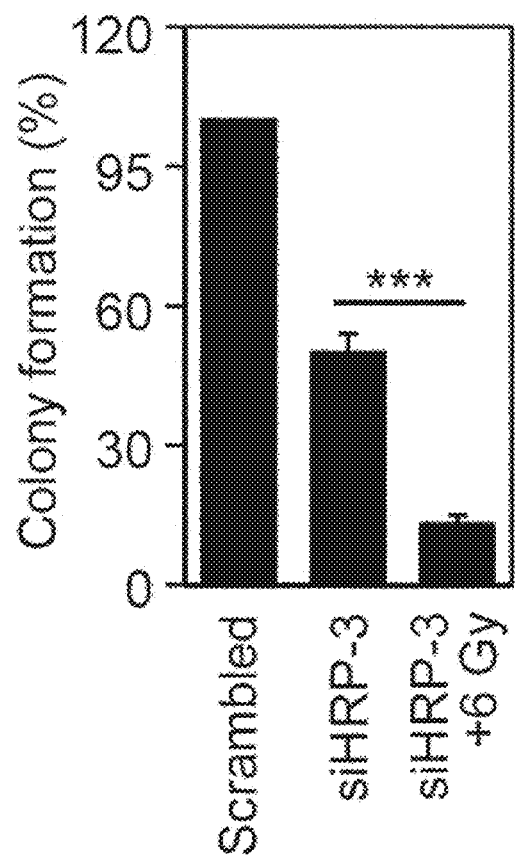

In order to examine whether HRP-3 is involved in responses to radiation or anticancer drugs, A549 cells were treated with 10 Gy radiation, 0.1 µg/ml doxorubicin or 5 ng/ml vinblastine and cultured for 48 hours, and then the level of HRP-3 protein in the cells was determined by Western blot analysis (FIG. 3A).

As shown in FIG. 3A, the level of HRP-3 in the cells treated with radiation or the drug peaked at about 24 hours, and then declined. This indicates that the level of HRP-3 protein has a correlation with radiation- or drug-resistance.

In order to examine this correlation, the effect of HRP-3 in the A549 cells treated with radiation or the drug was analyzed. Specifically, A549 cells were transfected with 100 nM scrambled siRNA or HRP-3 siRNA, and then treated with 10 Gy radiation, 0.1 µg/ml doxorubicin or 5 ng/ml vinblastine and cultured. The death rate of the cultured cells was determined by FACS analysis (FIG. 3B).

As shown in FIG. 3B, although siHRP-3 alone could induce apoptosis compared to control siRNA, a combination of siHRP-3 with radiation, doxorubicin or vinblastine significantly enhanced apoptosis by approximately 2.3-, 2.4- and 2.3-fold, respectively, compared to A549 cells transfected with siHRP-3 alone.

Next, A549 cells were transfected with 100 nM scrambled siRNA or HRP-3 siRNA, and then treated with 0 or 6 Gy of radiation while the cells were cultured for 14 days. The treated cells were subjected to a colony formation assay (FIGS. 3C and 3D). The survival fraction determined by the colony formation assay was presented as a survival curve.

As shown in FIGS. 3C and 3D, A549 cells subjected to both the inhibition of HRP-3 expression and radiation treatment showed decreased colony formation of about 74% compared to A549 cells treated with siHRP-3 alone, and the cells, where the expression of HRP-3 was inhibited, were more sensitive than control cells to exposure to 0 or 6 Gy of radiation.

Figure 3E:
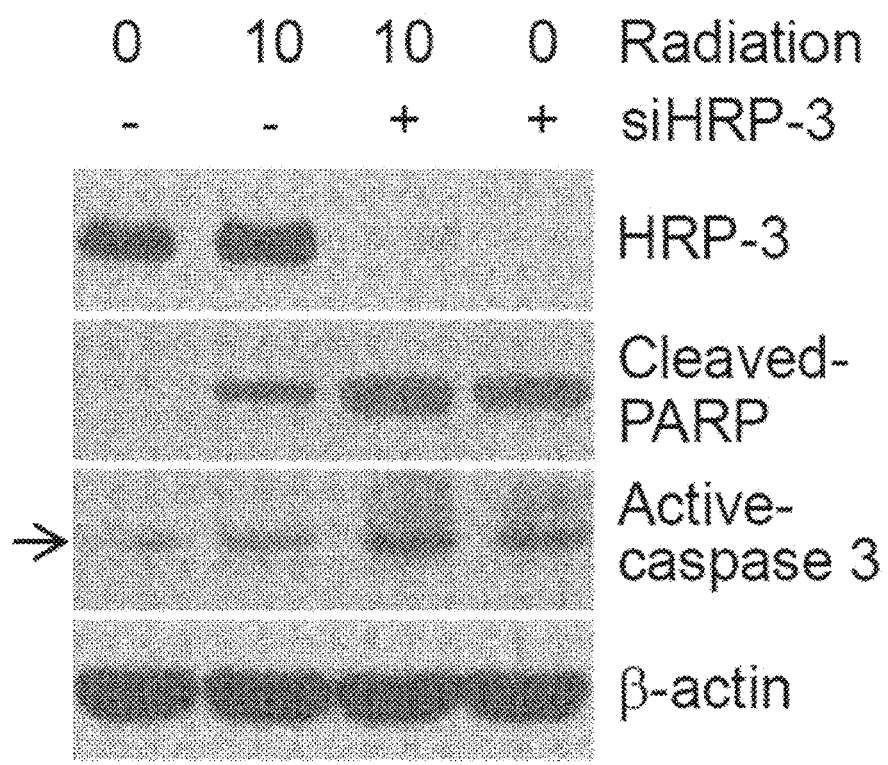
Figure 3F:
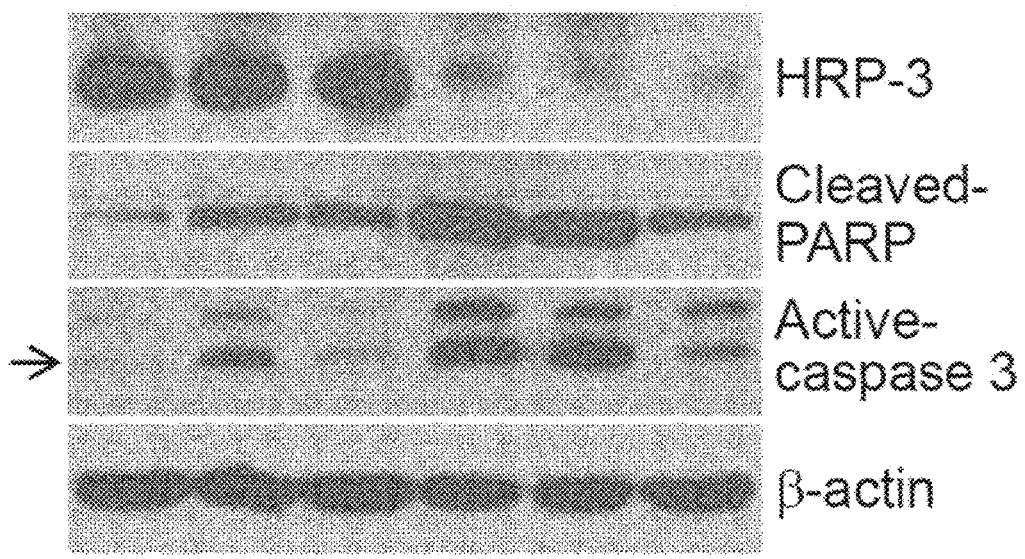

Additionally, A549 cells were transfected with 100 nM scrambled siRNA or HRP-3 siRNA, and then treated with 10 Gy radiation, 0.1 µg/ml doxorubicin or 5 ng/ml vinblastine for 48 hours, and the levels of two apoptotic markers (cleaved PARP and active caspase-3) in the cells were determined by Western blotting (FIGS. 3E and 3F).

As shown in FIGS. 3E and 3F, when the inhibition of HRP-3 expression was performed in combination with radiation or anticancer drug treatment, the levels of cleaved PARP and active caspase-3 significantly increased.

Taking the above results together, it can be seen that HRP-3 is a key molecule that regulates the sensitivity of radiation- and drug-resistant A549 cells to apoptosis.

Example 3

Effect of HRP-3 on ROS Production

In order to identify the mechanisms by which the inhibition of HRP-3 expression induces the apoptosis of A549 cells, the expression levels of ROS production-related molecules (Nrf2, HO-1, Keap-1 and HRP-3 proteins) were compared between H460 and A549 cells by Western blot analysis (FIG. 4A).

As shown in FIG. 4A, the expression level of HRP-3 was higher in A549 cells than in H460 cells, and the expression levels of antioxidant coordinators such as the transcription factor Nrf2 and its target HO-1 were higher in A549 cells than in H460 cells, but the expression level of Keap-1 protein that is an Nrf2 inhibitor was almost equal between the two types of cells.

The above results confirmed that HRP-3 can directly regulate the expression of Nrf2 and HO-1, and the following experiment was performed in order to verify this suggestion. Specifically, A549 cells were transfected with 100 nM scrambled siRNA or HRP-3 siRNA for 48 hours, and the expression levels of Nrf2, HO-1, Keap-1 and HRP-3 proteins in the cells were determined by Western blot analysis (FIG. 4B).

As shown in FIG. 4B, the protein levels of not only HRP-3 but also antioxidant coordinators such as the transcription factor Nrf2 and its target HO-1 were decreased by treatment with HRP-3 siRNA, but the level of Keap-1 was not changed.

The results indicate that the levels of Nrf2 and HO-1 are changed depending on the level of HRP-3 and that Nrf2/HO-1 signaling is a key antioxidant pathway that acts as a primary cellular defense system in response to oxidative stress. Thus, it was predicted that HRP-3 would influence ROS production, and the following experiment was performed in order to confirm this prediction. Specifically, A549 cells were transfected with 100 nM scrambled siRNA or HRP-3 siRNA and cultured for 48 hours in the presence or absence of 1 mM NAC as an ROS scavenger. The level of ROS produced in the cells was determined by FACS analysis using 10 nM DCF-DA (FIG. 4C).

As shown in FIG. 4C, the inhibition of HRP-3 expression in A549 cells induced an about 1.6-fold increase in ROS generation compared to control cells, which was reduced by treatment with NAC.

Further, A549 cells were transfected with 100 nM scrambled siRNA or HRP-3 siRNA without or with exposure to 10 Gy radiation and cultured, and the level of ROS produced in the cells was assessed by FACS analysis using 10 nM DCF-DA (FIG. 4D).

As shown in FIG. 4D, in radiation-treated A549 cells, the production of ROS increased by about 1.9 times, and in cells subjected to both the inhibition of HRP-3 expression and radiation treatment, the production of ROS significantly increased compared to that in control cells.

From these results, it can be seen that HRP-3 functions to eliminate ROS by Nrf2/HO-1 signaling.

Example 4

Effect of HRP-3 on ROS-dependent, p53-induced Apoptosis

Because the results of Example 3 indicated that HRP-3 functions to eliminate ROS, the present inventors focused on the tumor suppressor protein p53, a transcription factor activated by redox imbalance and DNA damage, in order to examine the effect of HRP-3 on ROS-dependent, p53-induced apoptosis.

Specifically, to examine the effect of ROS on p53-mediated apoptosis, the level of each protein was monitored after treatment with the ROS scavenger NAC. Specifically, A549 cells, untreated or treated with 1 mM NAC, were transfected with 100 nM scrambled siRNA or HRP-3 siRNA, and the expression levels of HRP-3, cleaved PARP, p53, phospho-p53(pp53) and PUMA proteins in the transfected cells were determined by Western blot analysis (FIGS. 5A and 5B).

As shown in FIGS. 5A and 5B, transfection of A549 cells with HRP-3-specific siRNA increased the expression and activation of p53 tumor-suppressor protein and also induced expression of PUMA, a key mediator of p53 dependent apoptosis, compared to controls. Also, the induction of cleaved PARP by HRP-3 deletion was significantly decreased by NAC treatment, suggesting a reduced commitment to apoptosis. Consistent with this notion, p53 and PUMA levels were also dramatically decreased by NAC treatment in siHRP-3-transfected A549 cells.

In addition, to determine whether HRP-3 deletion-mediated up-regulation of p53 protein is due to other factors, new protein synthesis was inhibited by treatment with 10 μM cycloheximide. Specifically, A549 cells were transfected with 100 nM scrambled siRNA or HRP-3 siRNA, and then treated with 10 μM cycloheximide for 1, 2, and 3 hours. The expression levels of HRP-3, cleaved PARP, p53, phospho-p53(pp53), and PUMA proteins in the treated cells were determined by Western blot analysis, the half-life (the time taken to reach 10% of the amount of biosynthetic protein by degradation) of the proteins was measured (FIG. 5C). Herein, the level of p53 mRNA was detected by RT-PCR using the following primers:

```
p53 (361 bp; annealing temperature: 55° C.;
28 cycles);

p53 F:
                                        (SEQ ID NO: 9)
5'-GTGGTGCCCTATGAGCCGCC-3';

p53 R:
                                        (SEQ ID NO: 10)
5'-GCTCACGCCCACGGATCTGA-3'.
```

As shown in FIG. 5C, the level of HRP-3 in A549 cells decreased with the passage of time to have a half-life of about 2 hours, and the level of p53 protein in A549 cells showed a short half-life within 1 hour. Deletion of cycloheximide or HRP-3 in A549 cells showed no particular effect on the level of p53 transcript, but the half-life of p53 protein was prolonged to at least 2 hours by HRP-3 deletion. Also, the half-life of pp53 was very similar to that of p53 when HRP-3 was not deleted, but it was prolonged to at least 3 hours when HRP-3 was deleted.

These results indicate that HRP-3 is involved in regulating p53 activation.

Additionally, the effect of p53 on the induction of apoptosis was examined. Specifically, A549 cells were transfected with 100 nM scrambled siRNA or HRP-3 siRNA, and then cultured without or with exposure to 10 Gy radiation for 48 hours. Next, the levels of HRP-3, cleaved PARP, p53, pp53, and PUMA proteins produced in the cells were detected by Western blot analysis (FIG. 5D).

As shown in FIG. 5D, during apoptotic apoptosis, p53 and PUMA were significantly increased in radiation-treated, HRP-3-deleted A549 cells compared with untreated cells or cells treated with radiation alone.

Such results indicate that p53 activated in response to ROS functions to induce apoptosis through its downstream target PUMA.

Example 5 p53-independent Effect of HRP-3

The results of Examples 1 to 4 indicate that, when HRP-3-deleted cells are treated with radiation, ROS produced thereby activates p53 and induces apoptosis through the downstream PUMA pathway of the activated p53. Thus, the effect of HRP-3-deletion in p53-depleted lung cancer cells was examined.

Example 5-1

Analysis of Correlation Between HRP-3 and Lung Cancer Using Database

In order to analyze the correlation between HRP-3 and lung cancer, Oncomine.™ (Compendia Bioscience, Ann Arbor, Mich.), a human genetic dataset analysis tool, was used. Specifically, to determine the expression levels of HRP-3 in cancer cells and normal cells, the alterations of HRP-3 in mRNA expression and DNA copy number change were analyzed using the database and compared between types of lung cancer (FIG. 6A).

FIG. 6A is a graphic diagram showing the expression levels of HRP-3 in normal cells and various types of lung cancer cells, analyzed through the Oncomine database (threshold p-value: 1E-4, and fold change: 2). In FIG. 6A, 0: normal cell, 1: lung adenocarcinoma cell, 2: lung carcinoid tumor cell, 3: small cell lung carcinoma cell, and 4: squamous cell carcinoma cell. As shown in FIG. 6A, the HRP-3 mRNA level was significantly higher in lung carcinoid tumor and small cell lung carcinoma, marginal in lung adenocarcinoma, and no different in squamous cell lung carcinoma compared to normal cells.

Such results indicate that the expression level of HRP-3 differs between types of lung cancer cells.

Example 5-2

Examination of Expression Level of HRP-3 in p53-depleted Cancer Line

An experiment was performed to examine the expression level of HRP-3 in H1299 lung cancer cells that express p53, not in A549 lung cancer cells that normally express p53, used in Examples 1 to 4.

Specifically, H1299, A549, and H460 cells that are Non-Small Cell Lung Cancer (NSCLC) cell lines were purchased from ATCC (Manassas, Va., USA) and cultured in RPMI-1640 medium.

Next, from total RNA collected from each type of the cultured cells, quantitative real-time PCR for HRP-3 was performed using a chromo 4 cycler, SYBR Premix Ex Taq™ (Takara Bio, Shiga, Japan) and synthesis primers according to a known method (H. S. Yun, et al., Biochem. Biophys. Res. Commun., 439:333-339, 2013) (top of FIG. 6B).

In addition, a cell lysate of each type of the cultured cells was analyzed by Western blotting using anti-HRP-3 antibody (Proteintech Group, Inc., Chicago, Ill., USA). Herein, β-actin was used as a loading control (bottom of FIG. 6B).

FIG. 6B shows graphs and images illustrating the results of measuring the expression levels of HRP-3 in three types of lung cancer cells (H1299 cells, A549 cells, and H460 cells), in which the top of FIG. 6B is a graphic diagram showing the results of quantitative real-time PCR, and the bottom is an image showing the results of Western blot analysis.

As shown in FIG. 6B, the transcript (top of FIG. 6B) and protein (bottom of FIG. 6B) levels of HRP-3 in lung cancer cell line H1299 cells that do not express p53 were higher than those in H460 cells, and similar to, or slightly lower than, those in A549 cells.

Because the results indicate that HRP-3 is highly expressed even in lung cancer cell lines that do not express p53, it is speculated that the p53-independent mechanisms of HRP-3 are present in addition to the above-identified p53-dependent mechanisms of HRP-3.

Example 5-3

Analysis of Intracellular Localization of HRP-3

Figure 6C:
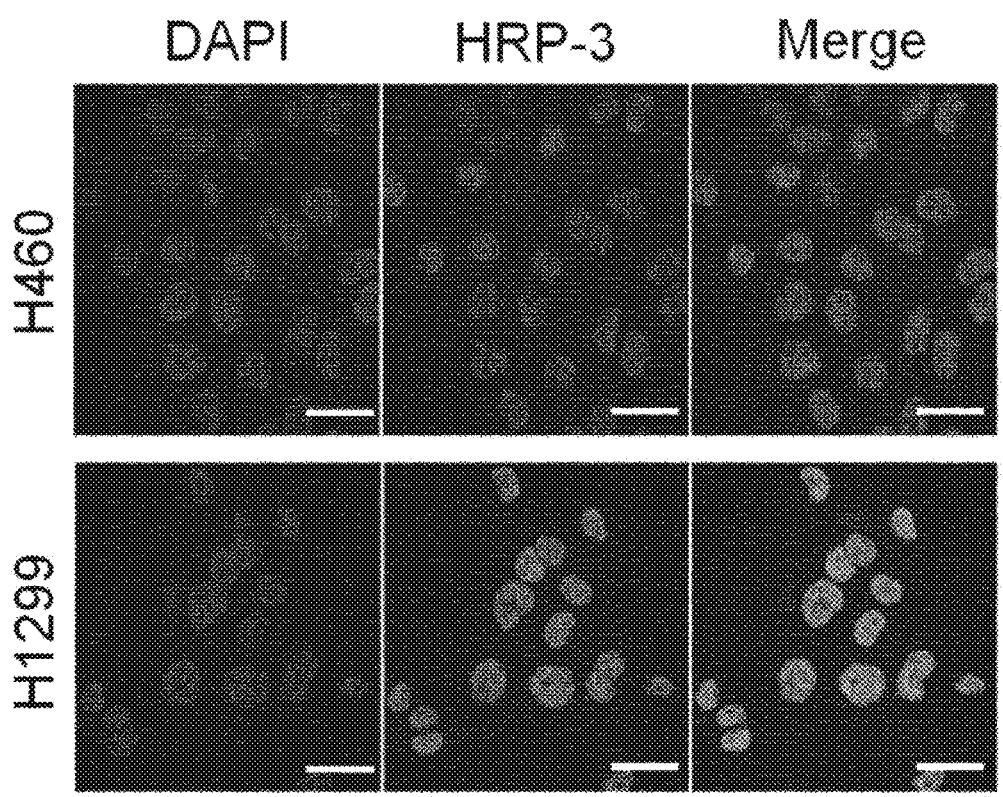

In order to examine HRP-3 localization in H1299 cells, immunofluorescence staining analysis was performed in the same manner as described in Example 1-3, except that H1299 lung cancer cells were used instead of A549 lung cancer cells (FIG. 6C).

FIG. 6C shows laser scanning confocal microscope images showing the results of immunofluorescence staining analysis performed to examine HRP-3 localization in H460 and H1299 cells. As shown in FIG. 6C, HRP-3 protein was localized only in the nucleus of H1299, consistent with the results obtained for A549 cells.

The above results confirmed that HRP-3 plays an important role in a signaling pathway that transmits external stimulus to the nucleus of cells to induce the response of the cells to the external stimulation.

Example 5-4

Effects of Radiation and Anticancer Agent Treatment on Expression Level of HRP-3

Figure 6D:
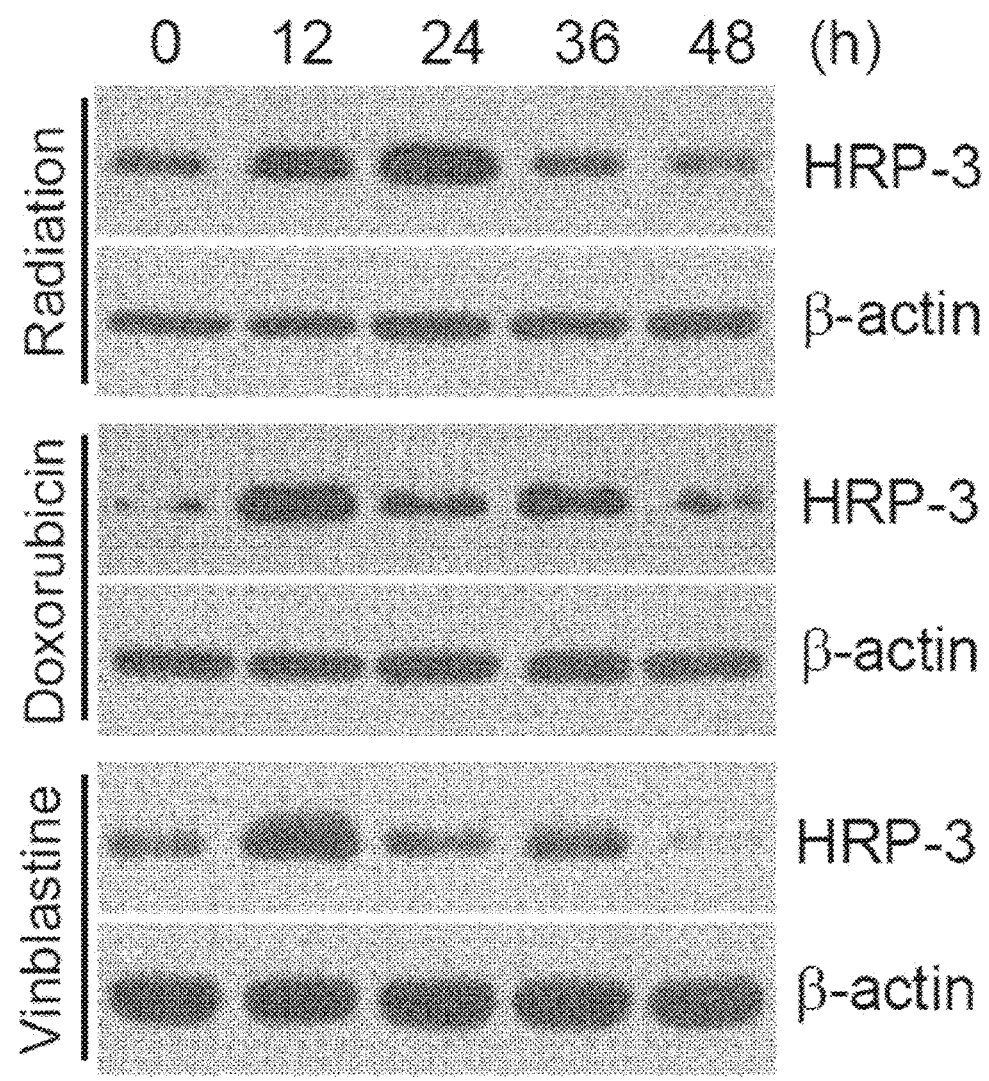
Figure 6E:
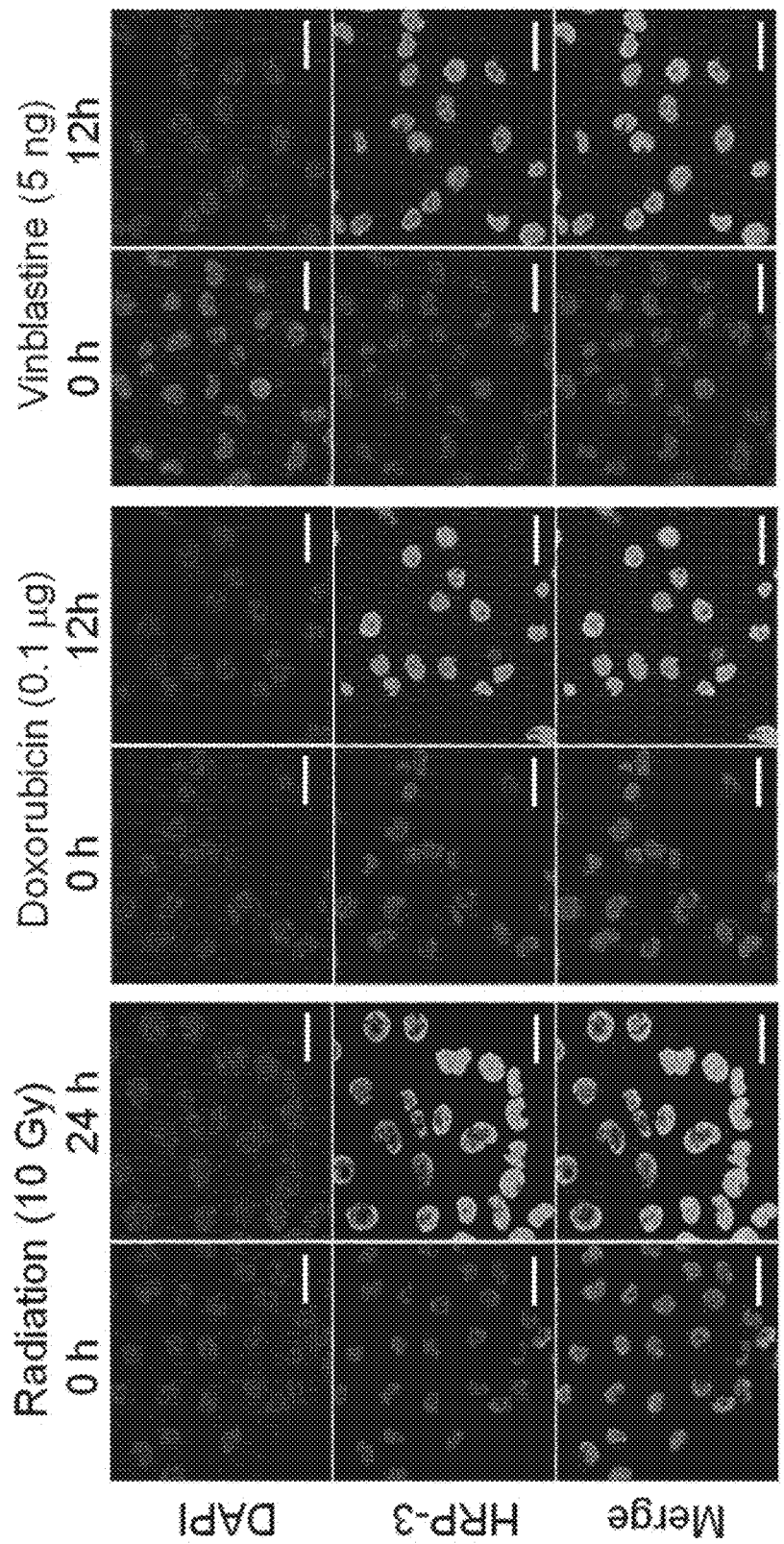

While H1299 cells were cultured in RPMI-1640 medium, the cells were radiated with 10 Gy of $^{137}$Cs-rays, or the cell culture was treated with 0.1 μg/ml doxorubicin or 5 ng/ml vinblastine, and the change in the expression level of HRP-3 as a function of time for a culture time of 48 hours was analyzed by Western blotting or immunofluorescence staining (FIGS. 6D and 6E).

FIG. 6D is an image showing the results of Western blot analysis performed to examine the change in HRP-3 protein level as a function of the culture time in the presence of radiation or anticancer agent treatment. As shown in FIG. 6D, in all cases, the expression level of HRP-3 significantly increased at 12-24 hours after treatment, and then gradually decreased. Specifically, when the cells were treated with radiation, the level of HRP-3 peaked at 24 hours after radiation, whereas, when the cells were treated with the anticancer drug (doxorubicin or vinblastine), the level of HRP-3 peaked at 12 hours after treatment.

The above results confirmed that the protein HRP-3 responds directly to radiation or anticancer drug treatment.

FIG. 6E shows images showing the results of immunofluorescence staining performed to examine the change in the intracellular localization of HRP-3 as a function of culture time in the presence of radiation or anticancer drug treatment (scale bar: 50 μm). As shown in FIG. 6E, even when the expression level of HRP-3 peaked by radiation or anticancer drug treatment, HRP-3 was still localized in the nucleus.

Although previous study results indicate that HRP-3 was switched from the nucleus to the cytoplasm in SMMC-7721 cells treated with epidermal growth factor, it could be seen that HRP-3 was not shifted by radiation or anticancer drug treatment at least in H1299 cells.

Taken together, the results in FIGS. 6A to 6E indicate that, although the expression level of HRP-3 differs between types of lung cancer cells, HRP-3 is highly expressed even in p53-depleted lung cancer cells, and the expressed HRP-3 is localized in the nucleus, and when the lung cancer cells are treated with radiation or anticancer cells, the expression level of HRP-3 significantly increases, but the intracellular localization thereof does not change.

Thus, it was predicted that HRP-3 would play a certain role in inducing resistance to external stimulation even in p53-depleted lung cancer cells.

Example 6

Analysis of Effect of a Combination of HRP-3 Depletion in p53-depleted Lung Cancer Cells with Anticancer Drug Treatment The effect of a combination of the inhibition of HRP-3 expression and anticancer treatment in H1299 cells that are p53-depleted lung cancer cells, was assessed in the following manner.

Example 6-1

Comparison of Anticancer Treatment Effects Against H460 Cells and H1299 Cells

While H460 cells and H1299 cells that are NSCLC cell lines, were cultured, these cells were subjected to anticancer treatment (radiation, doxorubicin, or vinblastine treatment), and then the apoptotic rate was compared between the two types of lung cancer cells.

Specifically, while each type of H460 cells and H1299 cells were inoculated into a culture dish at a density of 3.5×10$^5$ cells/cm$^2$ and cultured in RPMI-1640 medium, each type of cell was radiated with 0 and 10 Gy of $^{137}$Cs-rays, or the cell culture was treated with 0 and 0.1 μg/ml of doxorubicin or 0 and 5 ng/ml of vinblastine (Sigma, St. Louis, Mo., USA) and cultured. Next, the death rate of the cells was determined by FACS analysis according to a known method (M. J. Kim, et al., Cancer Lett, 339:15-24, 2013) (FIG. 7A).

FIG. 7A is a graphic diagram showing the results of comparing the death rates by anticancer treatments (radiation, doxorubicin treatment and vinblastine treatment) between H460 cells and H1299 cells. As shown in FIG. 7A, the H460 cells showed a apoptotic rate of about 41% by radiation, a apoptotic rate of about 39% by doxorubicin treatment, and a apoptotic rate of about 43% by vinblastine treatment, whereas the H1299 cells showed a apoptotic rate of about 20% by radiation, a apoptotic rate of about 23% by doxorubicin treatment, and a apoptotic rate of about 26% by vinblastine treatment.

The above results confirmed that H1299 cells show more significant resistance to anticancer treatment compared to H460 cells.

Example 6-2

Effect of HRP-3 on Proliferation of H1299 Cells

The effect of HRP-3 expression on cell proliferation was examined by inhibiting the expression of HRP-3 in H1299 cells while culturing the cells.

Specifically, H1299 cells were inoculated into a culture dish at a density of $3.5 \times 10^5$ cells/cm$^2$. The inoculated cells were transfected with 100 nM scrambled siRNA or HRP-3 siRNA (siHRP-3) for 5 hours, and then cultured in RPMI-1640 medium for 4 days, and the proliferation of the cells as a function of the culture time was measured and compared (FIG. 7B). Herein, the proliferation of the cells was measured by counting survival cells using a hemocytometer.

FIG. 7B is a graphic diagram showing the effect of HRP-3 expression on the proliferation of H1299 cells, in which (■) indicates H1299 cells treated with scrambled siRNA, and (▲) indicates H1299 cells treated with HRP-3 siRNA. As shown in FIG. 7B, HRP-3 expression in H1299 cells reduced cell proliferation in a culture time-dependent fashion.

The above results confirmed that HRP-3 plays an essential role in the survival of H1299 cells and that HRP-3 expression increases the possibility of induction of apoptosis in H1299 cells.

Example 6-3

Analysis of Correlation Between HRP-3 and Apoptosis in H1299 Cells

A cell lysate obtained by lysing the HRP-3 siRNA-treated H1299 cells cultured in Example 6-2 was analyzed by Western blotting using anti-HRP-3 antibody (Proteintech Group, Inc., Chicago, Ill., USA), anti-cleaved-PARP antibody (Asp214) and anti-caspase-3 antibody (Cell Signaling Technology Inc., Beverly, Mass., USA). Herein, β-actin was used as a loading control (FIG. 7C).

Figure 7C:
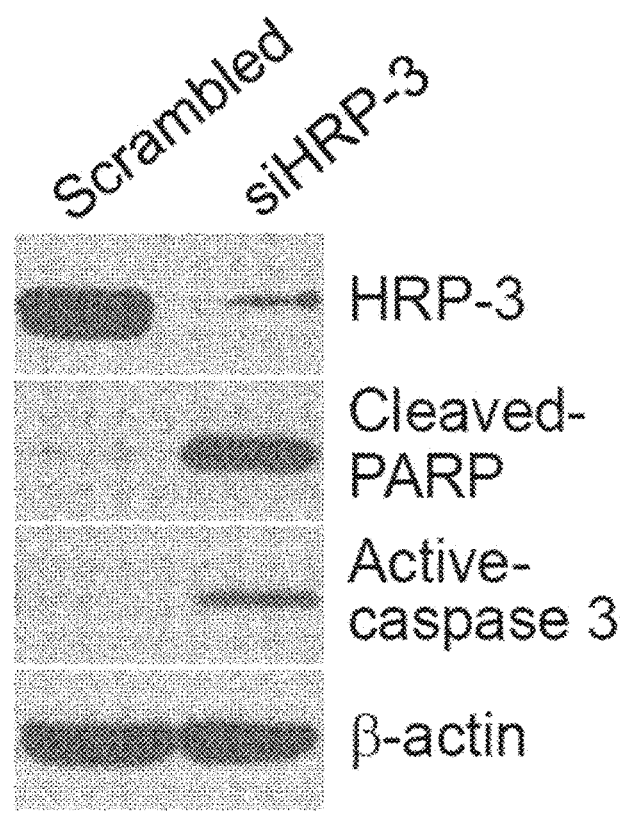

FIG. 7C is a Western blot image showing changes in the expression levels of leaved-PARP and active caspase-3, known as apoptotic markers, in H1299 cells, which were inhibited of HRP-3 expression. As shown in FIG. 7C, the expression levels of leaved-PARP and active caspase-3 (known as apoptotic markers) in H1299 cells, which were inhibited of HRP-3 expression, significantly increased.

The above results confirmed that the inhibition of HRP-3 expression in H1299 cells can induce apoptosis.

Example 6-4

Figure 7D:
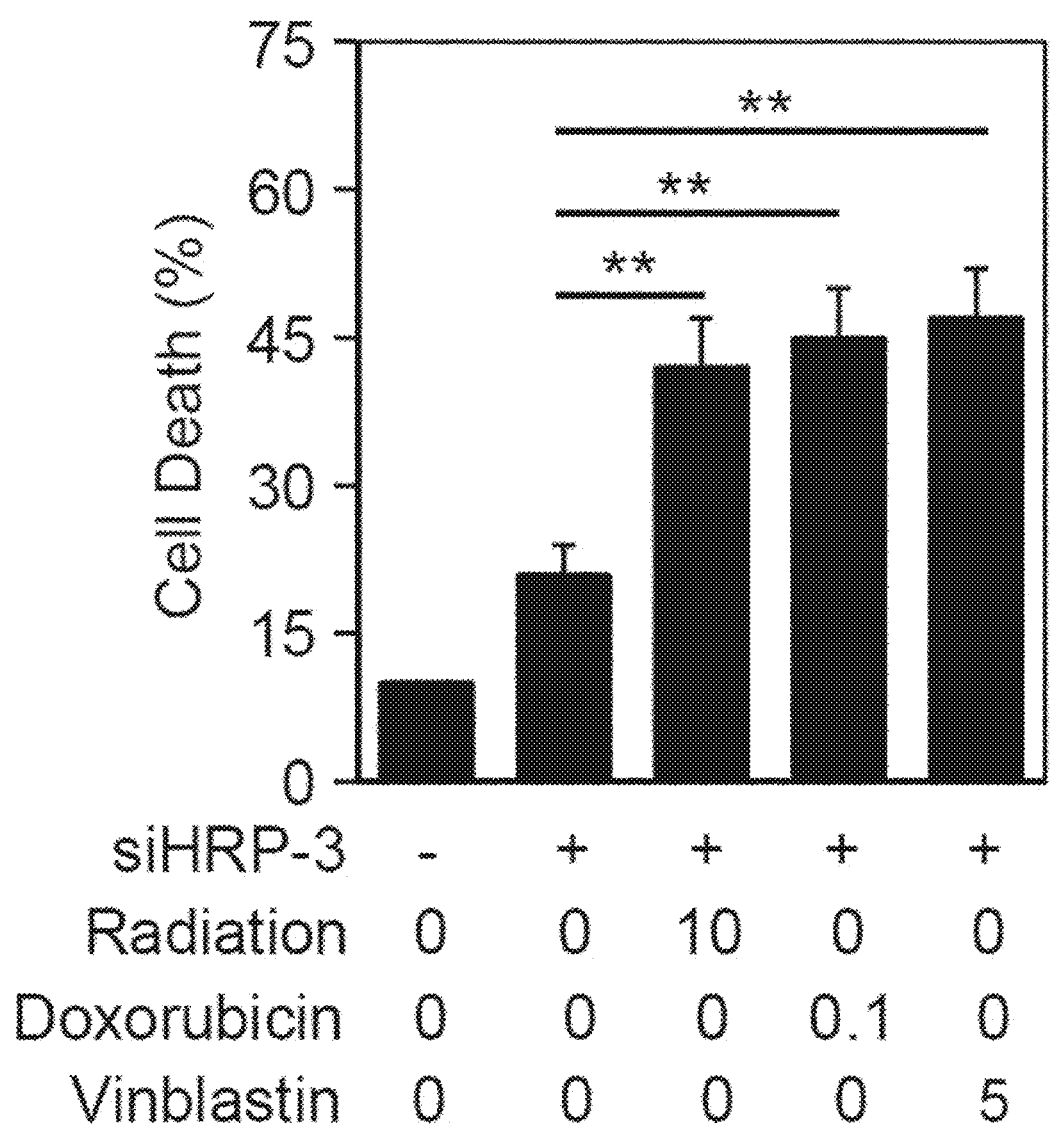
Figure 7E:
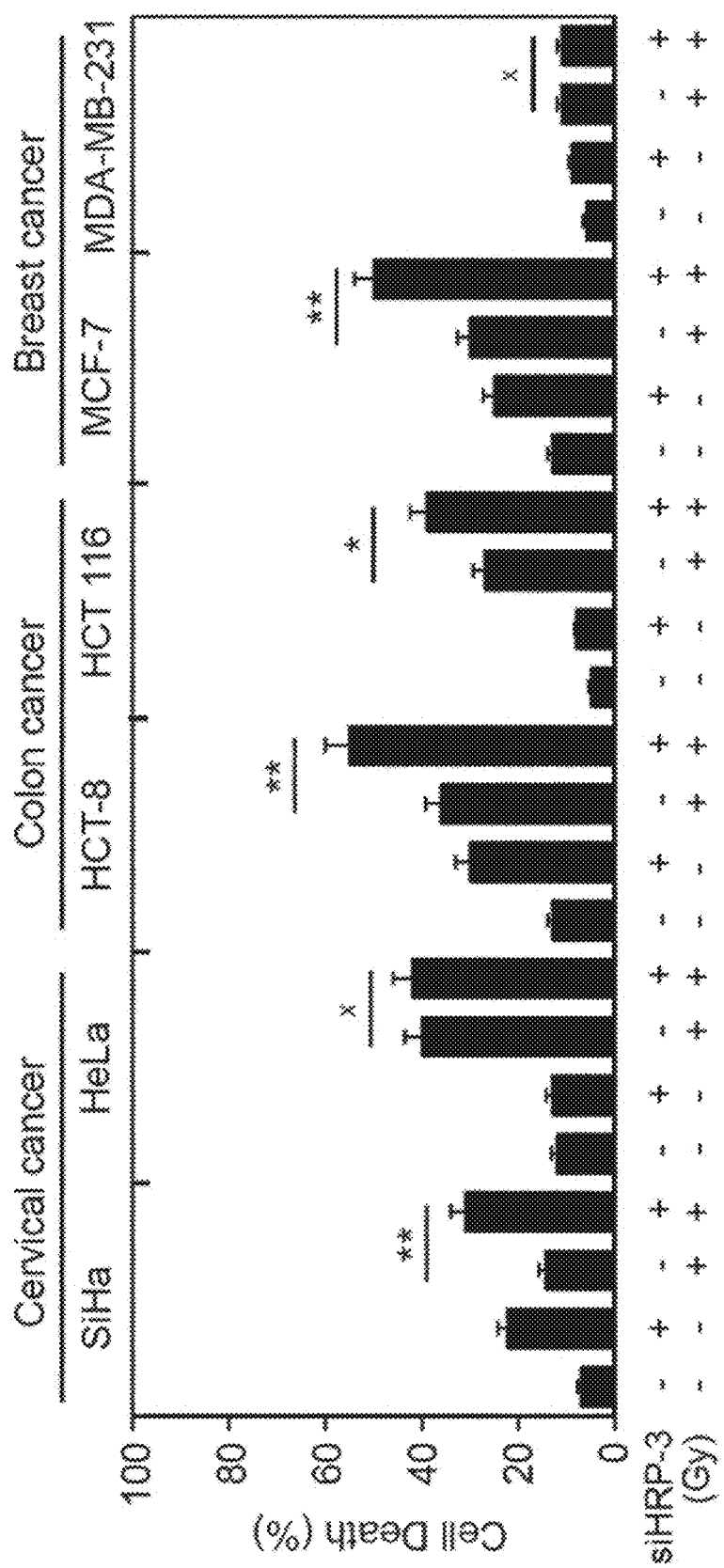

Effect of a Combination of the Inhibition of HRP-3 Expression in H1299 Cells with Anticancer Treatment The inhibition of HRP-3 expression in H1299 cells was performed according to the method in Example 6-2, and the H1299 cells, which were inhibited of HRP-3 expression, were subjected to anticancer treatment (radiation, doxorubicin treatment or vinblastine treatment), and their apoptotic rate was measured (FIG. 7D).

FIG. 7D is a graphic diagram showing a comparison of the apoptotic rate of the H1299 cells, where HRP expression was inhibited, between anticancer treatments (radiation, doxorubicin treatment, and vinblastine treatment). As shown in FIG. 7D, H1299 cells, which were inhibited of HRP-3 expression, showed an increase in apoptotic rate (about 21%) compared to the apoptotic rate of control cells (about 10%), and when the H1299 cells, which were inhibited of HRP-3 expression, were subjected to various anticancer treatments, the death rate of the cells was further increased (about 42% in radiation, about 45% in doxorubicin treatment, and about 47% in vinblastine treatment).

The above results demonstrate that the inhibition of HRP-3 expression is essential for anticancer treatment against H1299 cells.

Example 6-5

Effect of a Combination of the Inhibition of HRP-3 Expression in Other Cancer Cells with Radiation Because the results of Example 6-4 demonstrate that the inhibition of HRP-3 expression is essential for anticancer treatment against H1299 cells, whether this effect of the inhibition of HRP-3 expression can also be applied to other cancer cells was examined in the following manner.

Specifically, cervical cancer cell lines (SiHa and HeLa), colorectal cancer cell lines (HCT-8 and HCT 116), and breast cancer cell lines (MCF-7 and MDA-MB-231) were purchased from the ATCC. The SiHa and HeLa cell lines were cultured in DMEM medium containing 10% FBS, and the HCT-8, HCT 116, MCF-7 and MDA-MB-231 cell lines were cultured in RPMI-1640 medium.

The apoptotic rate was compared between the cell lines in the same manner as described in Example 6-4, except that the cultured SiHa, HeLa, HCT-8, HCT 116, MCF-7, and MDA-MB-231 cells were used instead of H1299 cells and that radiation alone was performed as anticancer treatment (FIG. 7E).

FIG. 7E is a graphic diagram showing a comparison of apoptotic rates between cervical cancer cell lines (SiHa and HeLa), colorectal cancer cell lines (HCT-8 and HCT 116), and breast cancer cell lines (MCF-7 and MDA-MB-231) after radiation, which were inhibited of HRP-3 expression. As shown in FIG. 7E, in the case of SiHa, HCT-8 and MCF-7 cells, the inhibition of HRP-3 expression increased the death rate of the cancer cells, and a combination of the inhibition of HRP-3 expression with radiation resulted in a further increase in death rate of the cancer cells, suggesting that the inhibition of HRP-3 expression and radiation lead to a synergistic effect. In the case of HCT 117 cells, the inhibition of HRP-3 expression alone resulted in no significant increase in death rate of the cancer cells, but a combination of the inhibition of HRP-3 expression with radiation resulted in a significant increase in death rate of the cancer cells. However, in the case of HeLa and MDA-MB-231 cells, the inhibition of HRP-3 expression resulted in no significant increase in death rate of the cancer cells, and a combination of the inhibition of HRP-3 expression with radiation also resulted in no significant increase in death rate of the cancer cells.

Such results demonstrate that the anticancer effect of the inhibition of HRP-3 expression varies depending on types of cancer cells.

Example 7

Analysis of Correlation Between ROS and the Inhibition of HRP-3 Expression

The Example intends to elucidate the correlation between the inhibition of HRP-3 expression and ROS that influences the apoptosis of H1299 cells, which were inhibited of HRP-3 expression.

Example 7-1

Effect of a Combination of the Inhibition of HRP-3 Expression in H1299 Cells with Radiation The morphological change and apoptotic rate of H1299 cells were measured in the same manner as described in Example 6-4, except that radiation alone was performed as anticancer treatment (FIG. 8A). Herein, the morphological change was observed with an optical microscope, and the apoptotic rate was measured by FACS analysis.

FIG. 8A shows an image (left; scale bar: 1 mm) illustrating the morphological change of H1299 cells subjected to a combination of the inhibition of HRP-3 expression and radiation, and a graph (right) illustrating the apoptotic rate of the cells. As shown in FIG. 8A, the inhibition of HRP-3 expression or radiation resulted in an increase in the apoptotic rate of H1299 cells, and a combination of the inhibition of HRP-3 expression with radiation resulted in a further increase in the apoptotic rate of H1299 cells.

Meanwhile, changes in the expression levels of cleaved-PARP and active caspase-3, known as apoptotic markers, were measured via Western blotting in the same manner as described in Example 6-3, except that each individual H1299 cell treated with the inhibition of HRP-3 expression, radiation, or a combination thereof was used instead of H1299 cells, which were inhibited of HRP-3 expression (FIG. 8B).

FIG. 8B is an image obtained by a Western blot showing changes in the expression levels of cleaved-PARP and active caspase-3 (known as apoptotic markers) in H1299 cells subjected to the inhibition of HRP-3 expression and radiation alone or a combination thereof. As shown in FIG. 8B, the levels of cleaved-PARP and active caspase-3 (known as apoptotic markers) increased in H1299 cells subjected to the inhibition of HRP-3 expression or radiation alone, and were the highest in H1299 cells subjected to a combination of the inhibition of HRP-3 expression and radiation simultaneously.

Example 7-2

Examination of Anticancer Mechanism of the Inhibition of HRP-3 Expression

In order to examine the correlation between the inhibition of HRP-3 expression and the increased apoptotic rate of H1299 cells, the expression levels of the transcription factor Nrf2 and its target HO-1, which are involved in the ROS production pathway, were measured.

A cell lysate obtained by lysing the scrambled siRNA or siHRP-3-treated H1299 cells cultured in Example 6-2 was analyzed by Western blotting using anti-HRP-3 antibody, anti-Nrf2 antibody (Santa Cruz Biotechnology Inc., Santa Cruz, Calif., USA), anti-Keap 1 antibody (R&D systems, Inc., Minneapolis, Minn., USA), and anti-HO-1 antibody (Cell Signaling Technology Inc., Beverly, Mass., USA). Herein, β-actin was used as a loading control (FIG. 8C).

Figure 8C:
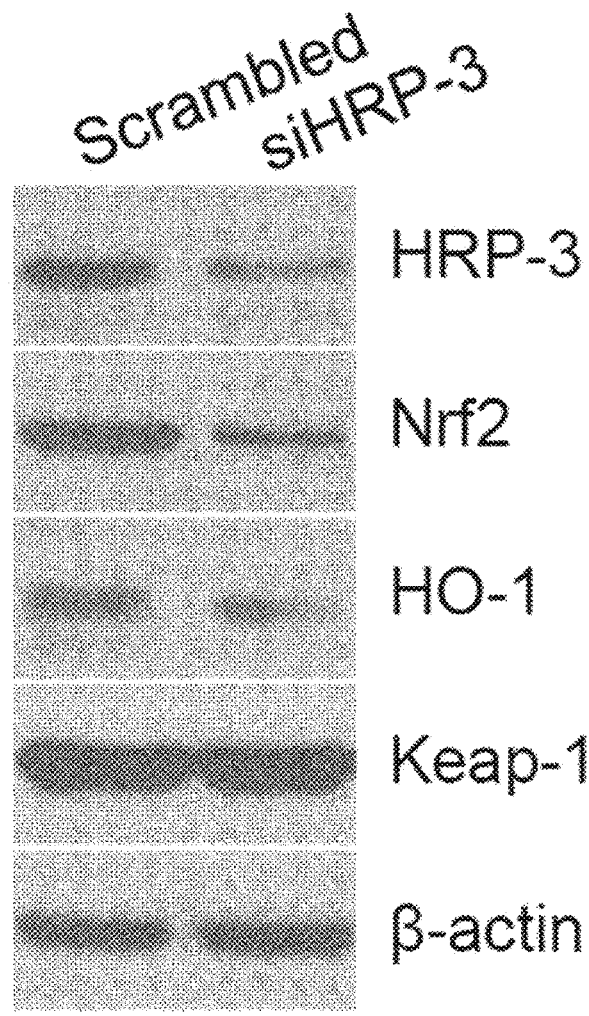
Figure 8D:
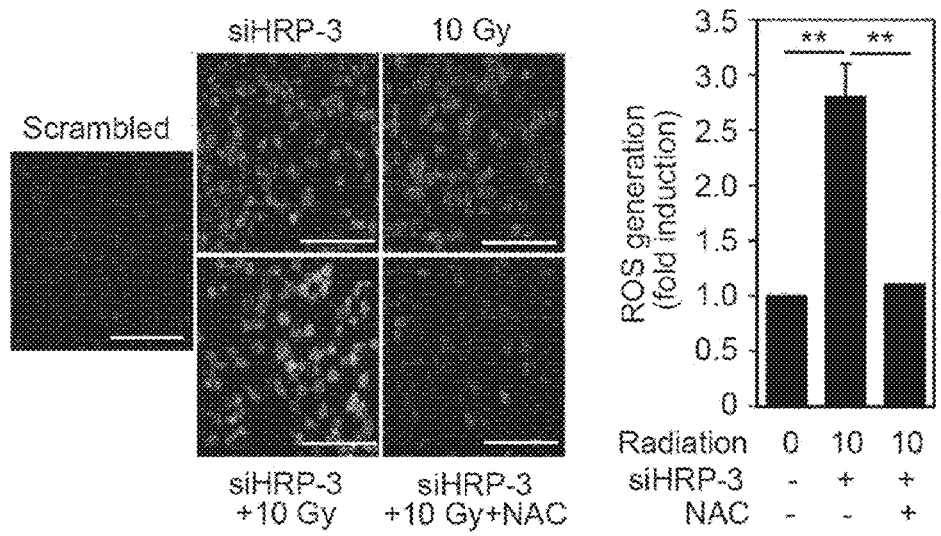
Figure 8E:
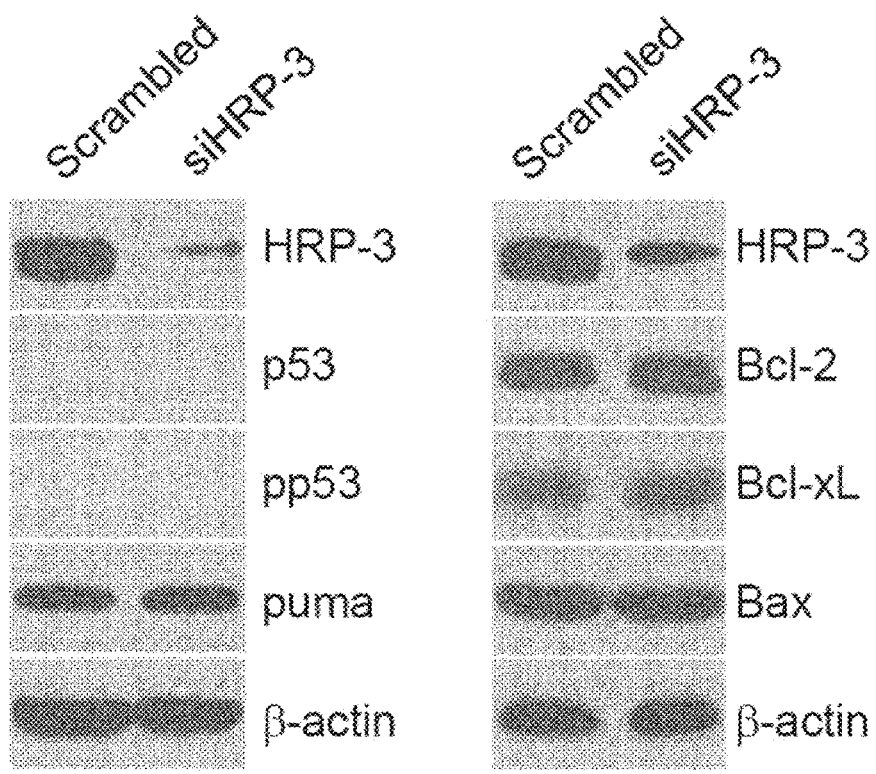

FIG. 8C is a Western blot image showing changes in the expression levels of the transcription factor Nrf2 and its target HO-1, which are involved in the ROS production pathway, in H1299 cells, which were inhibited of HRP-3 expression. As shown in FIG. 8C, the levels of Nrf2 and HO-1 proteins in H1299 cells, which were inhibited of HRP-3 expression, significantly decreased, although the expression level of Keap-1 (Nrf2 inhibitor) in the cells did not change.

The above results confirmed that the inhibition of HRP-3 expression induces the production of ROS through p53-independent Nrf2/HO-1 signaling.

Example 7-3

Effects of the Inhibition of HRP-3 Expression and ROS Elimination on Anticancer Treatment Against H1299 Cells H1299 cells subjected to the inhibition of HRP-3 expression, radiation and ROS elimination were obtained in the same manner as described in Example 7-1, except that H1299 cells were additionally treated with 3 mM NAC (N-acetyl cysteine) showing ROS-scavenging activity. According to a known method, the thus obtained H1299 cells were treated with 10 nM DCF-DA (2',7'-dichlorofluorescein diacetate) for 20 minutes, and the produced ROS was detected (M. J. Kim, et al., Cancer Lett, 339:15-24, 2013) (FIG. 8D). The detection of ROS was performed by observing the DCF-DA-stained cells with a laser scanning confocal microscope and analyzing the DCF-DA-stained cells by FACS analysis to determine the production of ROS.

FIG. 8D shows a laser scanning confocal microscope image (left; scale bar: 1 mm) and a graph (right) illustrating the results of the ROS production measured after the inhibition of HRP-3 expression and radiation. As shown in FIG. 8D, the ROS production significantly increased in H1299 cells subjected to the inhibition of HRP-3 expression and radiation (about 2.8 times compared to that of control cells), but the ROS production decreased to that of control cells when treated with NAC.

The results in FIG. 8D are consistent with those of Example 3 and demonstrate that HRP-3 functions to eliminate ROS even in p53-depleted lung cancer cells through Nrf2/HO-1 signaling.

Example 7-4

Analysis of Correlation Between the Inhibition of HRP-3 Expression and Other Signaling Pathways Based on the results of Example 7-3 confirming that HRP-3 serves to eliminate ROS, an experiment was performed to examine the effect of inhibiting HRP-3 expression on the expression of p53 signaling-related proteins activated by redox imbalance and DNA damage, and on the expression of Bcl-2 family proteins involved in apoptosis.

Specifically, a cell lysate obtained by lysing the scrambled siRNA- or siHRP-3-treated H1299 cells cultured in Example 6-2 was analyzed by Western blotting using anti-HRP-3 antibody, anti-p53 antibody (Santa Cruz Biotechnology Inc., Santa Cruz, Calif., USA), anti-phospho-p53 (Ser15) antibody (Cell Signaling Technology Inc., Beverly, Mass., USA) and anti-PUMA antibody (Cell Signaling Technology Inc., Beverly, Mass., USA). In addition, the same cell lysate was analyzed by Western blotting using anti-HRP-3 antibody, anti-Bcl-2 antibody (Santa Cruz Biotechnology Inc., Santa Cruz, Calif., USA), anti-Bcl-xl antibody (Santa Cruz Biotechnology Inc., Santa Cruz, Calif., USA) and anti-Bax antibody (Santa Cruz Biotechnology Inc., Santa Cruz, Calif., USA) (FIG. 8E). Herein, β-actin was used as a loading control (FIG. 8E).

FIG. 8E is a Western blot image showing changes in the expression levels of p53 signaling-related proteins (left) and apoptosis-related Bcl-2 family proteins (right) in H1299 cells, which were inhibited of HRP-3 expression. As shown in FIG. 8E, among p53 signaling-related proteins, p53 and phospho-p53 (pp53) were not expressed in H1299 cells regardless of the inhibition of HRP-3 expression, and the expression level of PUMA was not changed regardless of the inhibition of HRP-3 expression. In addition, the expression levels of apoptosis-related Bcl-2 family proteins were not changed, regardless of the inhibition of HRP-3 expression.

The above results confirmed that the inhibition of HRP-3 expression in H1299 cells have no association with p53 signaling-related proteins and Bcl-2 family proteins, and thus the increased ROS production by the inhibition of HRP-3 expression in H1299 cells are associated with other pathways.

Example 8

Analysis of Correlation Between the Inhibition of HRP-3 Expression and NF-κB Activation To examine the correlation between the inhibition of HRP-3 expression and the activation of the transcription factor NF-κB protein activated by the oxidation of ROS produced in H1299 cells, which were inhibited of HRP-3 expression, an experiment was performed as follows.

Example 8-1

Analysis of the Effect of the Inhibition of HRP-3 Expression on Activation of NF-κB The expression levels of IκB inhibiting NF-κB activation, c-Myc as a transcriptional target of NF-κB, and Noxa as a transcriptional target of c-Myc, and the activity of NF-κB were measured in H1299 cells, which were inhibited of HRP-3 expression.

Specifically, a cell lysate obtained by lysing the scrambled siRNA- or siHRP-3-treated H1299 cells cultured in Example 6-2 was analyzed by Western blot using anti-HRP-3 antibodies, anti-IκB antibodies (Santa Cruz Biotechnology Inc., Santa Cruz, Calif., USA), anti-c-Myc antibodies (Calbiochem, San Diego, Calif., USA) and anti-Noxa antibodies (Calbiochem, San Diego, Calif., USA). Herein, β-actin was used as a loading control (FIG. 9A; left). As control cells, H1299 cells were treated with scrambled siRNA alone.

In addition, the activity of NF-κB in the scrambled siRNA- or siHRP-3-treated H1299 cells was measured by a reporter gene assay using Dual-Reporter™. Specifically, H1299 cells were transfected with 0.5 μg plasmid DNA (pNF-κB-luc; Stratagene, Cambridge, UK) in Dual-Reporter™, and then the luciferase activity in the cells was measured using a luminometer, and the activity of NF-κB was measured at various protein concentrations (FIG. 9A; right).

FIG. 9A shows an image illustrating the results of the expression levels of NF-κB activity-related IκB, c-Myc, and Noxa in H1299 cells measured by Western blot analysis, and also a graph illustrating the results of measuring NF-κB activity in the cells by a reporter gene assay. As shown in FIG. 9A, the inhibition of HRP-3 expression in H1299 cells resulted in a decrease in the expression level of IκB, whereas the inhibition of HRP-3 expression in H1299 cells resulted in an increase in the expression levels of c-Myc and Noxa and an about 1.8-fold increase in NF-κB activity.

The above results confirmed that the inhibition of HRP-3 expression in H1299 cells can induce an increase in NF-κB activity.

Example 8-2

Analysis of the Effects of the Inhibition of HRP-3 Expression and Radiation on NF-κB Activation H1299 cells subjected to the inhibition of HRP-3 expression and radiation were obtained in the same manner as described in Example 6-4, except that radiation alone, was performed as anticancer treatment. The thus obtained H1299 cells were lysed to obtain a cell lysate. The expression levels of IκB, c-Myc and Noxa were measured in the same manner as described in Example 8-1, except that the thus obtained lysate was used, and NF-κB activity was also measured in the same manner as described in Example 8-1 (FIG. 9B). As control cells, H1299 cells treated with scrambled siRNA alone were used.

FIG. 9B shows an image(left) illustrating the results of the expression levels of NF-κB activity-related IκB, c-Myc and Noxa in radiation-treated H1299 cells, which were inhibited of HRP-3 expression, analyzed by Western blot analysis, and also a graph (right) illustrating the results of measuring NF-κB activity analyzed by a reporter gene assay. As shown in FIG. 9B, the inhibition of HRP-3 expression in H1299 cells decreased the expression level of IκB regardless of radiation, whereas the expression levels of c-Myc and Noxa were increased by radiation, and the highest expression level was shown in the cells subjected to both the inhibition of HRP-3 expression and radiation simultaneously. In addition, NF-κB activity was also increased by the inhibition of HRP-3 expression or radiation, and was the highest when the cells were subjected to both the inhibition of HRP-3 expression and radiation simultaneously.

The above results confirmed that NF-κB activity is directly involved in the anticancer effects by the inhibition of HRP-3 expression and radiation.

Example 8-3

Analysis of the Effect of Inhibition of ROS Production on NF-κB Activation

H1299 cells subjected to the inhibition of HRP-3 expression and ROS elimination were obtained in the same manner as described in Example 8-1, except that H1299 cells were additionally treated with 3 mM of NAC (N-acetyl cysteine) showing ROS scavenging activity. The thus obtained cells were lysed to obtain a cell lysate. The expression levels of IκB, c-Myc and Noxa were measured by Western blot analysis in the same manner as described in Example 8-1, except that the cell lysate was used. Also, NF-κB activity was measured by a reporter gene assay (FIG. 9C). As control cells, H1299 cells treated with scrambled siRNA alone were used.

FIG. 9C shows an image (left) illustrating the results of measuring the expression levels of NF-κB activity-related IκB, c-Myc and Noxa in H1299 cells, subjected to the inhibition of HRP-3 expression and inhibition of ROS production, by Western blot analysis, and also a graph (right) showing the results of measuring NF-κB activity by a reporter gene assay. As shown in FIG. 9C, the inhibition of HRP-3 expression in H1299 cells resulted in a decrease in the expression level of IκB, but an increase in the expression levels of c-Myc and Noxa and an increase in NF-κB activity. However, when H1299 cells were subjected to both the inhibition of HRP-3 expression and inhibition of ROS production simultaneously, it led to the inhibition of the decrease in the expression level of IκB, the increase in the expression levels of c-Myc and Noxa, and the increase in NF-κB activity in the cells due to the inhibition of HRP-3 expression, thus showing levels similar to the control cells.

The above results confirmed that the increase in NF-κB activity due to the inhibition of HRP-3 expression in H1299 cells can be regulated depending on the production of ROS.

Example 8-4

Analysis of the Effect of BAY on NF-κB Activation

H1299 cells subjected to the inhibition of HRP-3 expression and ROS elimination were obtained in the same manner as described in Example 8-1, except that H1299 cells were additionally treated with 2 μM of BAY 11-7082 (BAY; Calbiochem, San Diego, Calif., USA) that inhibits NF-κB activity. The thus obtained cells were lysed to obtain a cell lysate. The expression levels of IκB, c-Myc and Noxa were measured by Western blot analysis in the same manner as described in Example 8-1, except that the cell lysate was used. Also, NF-κB activity in the cells was measured by a reporter gene assay (FIG. 9D). As control cells, H1299 cells treated with scrambled siRNA alone were used.

FIG. 9D shows an image (left) illustrating the results of measuring the expression levels of IκB, c-Myc and Noxa in H1299 cells, subjected to the inhibition of HRP-3 expression and inhibition of NF-κB activity, by Western blot analysis, and also a graph (right) illustrating NF-κB activity in the cells by a reporter gene assay. As shown in FIG. 9D, the inhibition of HRP-3 expression in H1299 cells led to a decrease in the expression level of IκB, but an increase in the expression levels of c-Myc and Noxa, and NF-κB activity. However, when H1299 cells were subjected to both the inhibition of HRP-3 expression and inhibition of NF-κB activity simultaneously, it led to the inhibition of the decrease in the expression level of IκB, the increase in the expression levels of c-Myc and Noxa, and the increase in NF-κB activity in the cells due to the inhibition of HRP-3 expression, thus showing levels similar to the control cells.

The above results confirmed that the inhibition of HRP-3 expression in H1299 cells can result in increased NF-κB activity, which activates downstream c-Myc and Noxa signaling pathways, thereby inducing apoptosis of the H1299 cells.

Taken together, the results of Examples 8-1 to 8-4 confirmed that the inhibition of HRP-3 expression in cancer cells that express no p53 can induce increased ROS production, leading to increased NF-κB activity, which activates downstream c-Myc and Noxa signaling pathways, thereby inducing apoptosis of the cancer cells.

The invention claimed is:

1. A method for treating a radiation- or drug-resistant lung cancer comprising administering a pharmaceutically effective amount of a pharmaceutical composition comprising an agent capable of inhibiting the expression of hepatoma-derived growth factor (HDGF)-related protein-3 (HRP-3) to a subject having the radiation- or drug-resistant lung cancer,
wherein the agent comprises an siRNA that binds to a HRP-3 mRNA to degrade the HRP-3 mRNA, wherein the siRNA comprises the sequences as set forth in SEQ ID NO: 7 and SEQ ID NO: 8.

2. The method of claim 1, wherein the radiation- or drug-resistant lung cancer exhibits resistance to radiation treatment or anticancer drug treatment due to overexpression of the HRP-3.

3. The method of claim 1, wherein the radiation- or drug-resistant lung cancer is non-small-cell lung cancer which overexpresses HRP-3.

4. The method of claim 1, wherein the composition is used in combination with radiation or an anticancer drug.

5. The method of claim 4, wherein the anticancer drug is selected from the group consisting of doxorubicin, vinblastine, taxol, etoposide, cisplatin, 5-FU, ifosfamide, and a combination thereof.

6. The method of claim 1, wherein the composition further comprises a pharmaceutically acceptable carrier, an excipient, or a diluent.

7. The method of claim 1, wherein the composition has an effect of inducing reactive oxygen species (ROS)-dependent activation of p53.

8. The method of claim 1, wherein the composition has an effect of inducing reactive oxygen species (ROS)-dependent activation of NF-kappa B.

9. A method for removing or attenuating a radiation- or drug-resistance of a lung cancer comprising administering a pharmaceutically effective amount of a pharmaceutical composition comprising an agent capable of inhibiting the expression of a hepatoma-derived growth factor (HDGF)-related protein-3 (HRP-3) to a subject having the radiation- or drug-resistant lung cancer,
wherein the agent comprises an siRNA that binds to a HRP-3 mRNA to degrade the HRP-3 mRNA, wherein the siRNA comprises the sequences as set forth in SEQ ID NO: 7 and SEQ ID NO: 8.

10. A method for removing or attenuating a radiation- or drug-resistance of a lung cancer cell comprising introducing an agent capable of inhibiting the expression of a hepatoma-derived growth factor (HDGF)-related protein-3 (HRP-3) into the radiation- or drug-resistant lung cancer cell,
wherein the agent comprises an siRNA that binds to a HRP-3 mRNA to degrade the HRP-3 mRNA, wherein the siRNA comprises the sequences as set forth in SEQ ID NO: 7 and SEQ ID NO: 8.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: HRP-3 F primer

<400> SEQUENCE: 1
atgaagggct acccgcactg                                                   20

<210> SEQ ID NO 2
<211> LENGTH: 22
<212> TYPE: DNA
<213> ORGANISM: Artificial Sequence
<220> FEATURE:
<223> OTHER INFORMATION: HRP-3 R primer

<400> SEQUENCE: 2
ccgggactgt ttagaggatt tc                                                22

<210> SEQ ID NO 3
<211> LENGTH: 21
<212> TYPE: DNA
<213> ORGANISM: Artificial Sequence
<220> FEATURE:
<223> OTHER INFORMATION: GAPDH F primer

<400> SEQUENCE: 3
catctctgcc ccctctgctg a                                                 21

<210> SEQ ID NO 4
<211> LENGTH: 21
<212> TYPE: DNA
<213> ORGANISM: Artificial Sequence
<220> FEATURE:
<223> OTHER INFORMATION: GAPDH R primer
```

<400> SEQUENCE: 4
ggatgacctt gcccacagcc t					21

<210> SEQ ID NO 5
<211> LENGTH: 21
<212> TYPE: RNA
<213> ORGANISM: Artificial Sequence
<220> FEATURE:
<223> OTHER INFORMATION: HRP-3 siRNA #1 F

<400> SEQUENCE: 5
ccagugaagg gaccuaacuu u					21

<210> SEQ ID NO 6
<211> LENGTH: 21
<212> TYPE: RNA
<213> ORGANISM: Artificial Sequence
<220> FEATURE:
<223> OTHER INFORMATION: HRP-3 siRNA #1 R

<400> SEQUENCE: 6
aguuaggucc cuucacuggu u					21

<210> SEQ ID NO 7
<211> LENGTH: 21
<212> TYPE: RNA
<213> ORGANISM: Artificial Sequence
<220> FEATURE:
<223> OTHER INFORMATION: HRP-3 siRNA #2 F

<400> SEQUENCE: 7
ggccaugugu aaaguuuaau u					21

<210> SEQ ID NO 8
<211> LENGTH: 21
<212> TYPE: RNA
<213> ORGANISM: Artificial Sequence
<220> FEATURE:
<223> OTHER INFORMATION: HRP-3 siRNA #2 R

<400> SEQUENCE: 8
uuaaacuuua cacauggccu u					21

<210> SEQ ID NO 9
<211> LENGTH: 20
<212> TYPE: DNA
<213> ORGANISM: Artificial Sequence
<220> FEATURE:
<223> OTHER INFORMATION: p53 F primer

<400> SEQUENCE: 9
gtggtgccct atgagccgcc					20

<210> SEQ ID NO 10
<211> LENGTH: 20
<212> TYPE: DNA
<213> ORGANISM: Artificial Sequence
<220> FEATURE:
<223> OTHER INFORMATION: p53 R primer

<400> SEQUENCE: 10
gctcacgccc acggatctga					20